(12) United States Patent
Gross et al.

(10) Patent No.: US 8,926,695 B2
(45) Date of Patent: Jan. 6, 2015

(54) SEGMENTED RING PLACEMENT

(75) Inventors: Amir Gross, Tel-Aviv (IL); Iftah Beinart, Hod Hasharon (IL); Eliahu Eliachar, Haifa (IL); Nir Lilach, Kfar Yehoshua (IL); Ram Grossfeld, Haifa (IL); Dmitry Golom, Haifa (IL); Gideon Meyer-Brodnitz, Haifa (IL); Arnon Mosaiuf, Geva Carmel (IL)

(73) Assignee: ValTech Cardio, Ltd. (IL)

( * ) Notice: Subject to any disclaimer, the term of this patent is extended or adjusted under 35 U.S.C. 154(b) by 0 days.

(21) Appl. No.: 11/950,930

(22) Filed: Dec. 5, 2007

(65) Prior Publication Data
US 2008/0262609 A1    Oct. 23, 2008

Related U.S. Application Data

(60) Provisional application No. 60/873,075, filed on Dec. 5, 2006, provisional application No. 60/902,146, filed on Feb. 16, 2007, provisional application No. 61/001,013, filed on Oct. 29, 2007.

(51) Int. Cl.
| | |
|---|---|
| A61F 2/24 | (2006.01) |
| A61B 17/064 | (2006.01) |
| A61B 17/068 | (2006.01) |
| A61B 17/00 | (2006.01) |

(52) U.S. Cl.
CPC .......... *A61F 2/2445* (2013.01); *A61B 17/064* (2013.01); *A61B 17/068* (2013.01); *A61F 2/2466* (2013.01); *A61B 2017/00783* (2013.01); *A61B 2017/0649* (2013.01); *A61F 2250/006* (2013.01)
USPC ........................................ 623/2.36; 623/2.37

(58) Field of Classification Search
USPC ............................................... 623/2.36, 2.37
See application file for complete search history.

(56) References Cited

U.S. PATENT DOCUMENTS

| 3,604,488 A | 9/1971 | Wishart et al. |
| 3,656,185 A | 4/1972 | Carpentier |

(Continued)

FOREIGN PATENT DOCUMENTS

| CN | 101653365 A | 2/2010 |
| WO | 9205093 | 4/1992 |

(Continued)

OTHER PUBLICATIONS

Odell JA et al., "Early results of a simplified method of mitral valve annuloplasty", Circulation 92: 150-154, 1995.

(Continued)

*Primary Examiner* — Thomas J Sweet
*Assistant Examiner* — Matthew Schall
(74) *Attorney, Agent, or Firm* — Cantor Colburn LLP

(57) ABSTRACT

Apparatus is provided for repairing a valve of a patient, the valve including an annulus and at least first and second leaflets. The apparatus includes at least a first discrete segment and a second discrete segment of an annuloplasty structure, each segment being shaped to provide a respective lateral wall, each lateral wall being shaped to define at least one lumen of the respective segment. The apparatus further includes at least a first and a second control wire, each control wire configured for sliding advancement through both the first and second segments. The first control wire is configured to control a relative disposition of a first end of the first segment and a first end of the second segment. The second control wire is configured to control a relative disposition of a second end of the first segment and a second end of the second segment. Other embodiments are also described.

28 Claims, 18 Drawing Sheets

(56) References Cited

U.S. PATENT DOCUMENTS

| | | |
|---|---|---|
| 3,840,018 A | 10/1974 | Heifetz |
| 3,898,701 A | 8/1975 | La Russa |
| 4,042,979 A | 8/1977 | Angell |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 5,061,277 A | 10/1991 | Carpentier et al. |
| 5,104,407 A | 4/1992 | Lam et al. |
| 5,108,420 A | 4/1992 | Marks |
| 5,201,880 A | 4/1993 | Wright et al. |
| 5,306,296 A | 4/1994 | Wright et al. |
| 5,450,860 A | 9/1995 | O'Connor |
| 5,477,856 A | 12/1995 | Lundquist |
| 5,593,424 A | 1/1997 | Northrup, III |
| 5,601,572 A | 2/1997 | Middleman et al. |
| 5,669,919 A | 9/1997 | Sanders et al. |
| 5,674,279 A | 10/1997 | Wright et al. |
| 5,683,402 A | 11/1997 | Cosgrove et al. |
| 5,709,695 A | 1/1998 | Northrup, III |
| 5,716,397 A | 2/1998 | Myers |
| 5,843,120 A | 12/1998 | Israel et al. |
| 5,855,614 A | 1/1999 | Stevens et al. |
| 5,876,373 A | 3/1999 | Giba et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,217,610 B1 | 4/2001 | Carpentier et al. |
| 6,251,092 B1 | 6/2001 | Qin et al. |
| 6,315,784 B1 | 11/2001 | Djurovic |
| 6,319,281 B1 | 11/2001 | Patel |
| 6,332,893 B1 | 12/2001 | Mortier et al. |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,451,054 B1 | 9/2002 | Stevens |
| 6,503,274 B1 | 1/2003 | Howanec, Jr. et al. |
| 6,524,338 B1 | 2/2003 | Gundry |
| 6,537,314 B2 | 3/2003 | Langberg et al. |
| 6,547,801 B1 | 4/2003 | Dragent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,711,444 B2 | 3/2004 | Koblish |
| 6,718,985 B2 | 4/2004 | Hlavka et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Golfarb et al. |
| 6,764,510 B2 | 7/2004 | Vidlund et al. |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,964,684 B2 | 11/2005 | Ortiz et al. |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,077,862 B2 | 7/2006 | Vidlund et al. |
| 7,101,395 B2 | 9/2006 | Tremulin et al. |
| 7,112,207 B2 | 9/2006 | Allen et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,226,467 B2 | 6/2007 | Lucatero et al. |
| 7,226,477 B2 | 6/2007 | Cox |
| 7,238,191 B2 | 7/2007 | Bachmann |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,280 B2 | 2/2008 | Bolling et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,507,252 B2 | 3/2009 | Lashinski et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,563,267 B2 | 7/2009 | Goldfarb et al. |
| 7,563,273 B2 | 7/2009 | Goldfarb et al. |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,632,303 B1 | 12/2009 | Stalker et al. |

(56) References Cited

U.S. PATENT DOCUMENTS

| | | |
|---|---|---|
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,699,892 B2 | 4/2010 | Rafiee et al. |
| 7,927,371 B2 | 4/2011 | Navia et al. |
| 7,988,725 B2 | 8/2011 | Gross et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,034,103 B2 | 10/2011 | Burriesci et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,800 B2 | 2/2012 | McCarthy et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,226,711 B2 | 7/2012 | Mortier et al. |
| 8,231,671 B2 | 7/2012 | Kim |
| 8,241,351 B2 | 8/2012 | Cabiri |
| 8,252,050 B2 | 8/2012 | Maisano et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,353,956 B2 | 1/2013 | Miller et al. |
| 8,357,195 B2 | 1/2013 | Kuehn |
| 8,382,829 B1 | 2/2013 | Call et al. |
| 8,430,926 B2 | 4/2013 | Kirson |
| 8,500,800 B2 | 8/2013 | Maisano et al. |
| 8,523,881 B2 | 9/2013 | Cabiri et al. |
| 8,523,940 B2 | 9/2013 | Richardson et al. |
| 8,545,553 B2 | 10/2013 | Zipory et al. |
| 8,591,576 B2 | 11/2013 | Hasenkam et al. |
| 2001/0021874 A1 | 9/2001 | Carpentier |
| 2002/0029080 A1 | 3/2002 | Mortier et al. |
| 2002/0042621 A1 | 4/2002 | Liddicoat et al. |
| 2002/0087048 A1 | 7/2002 | Brock et al. |
| 2002/0103532 A1 | 8/2002 | Langberg et al. |
| 2002/0173841 A1 | 11/2002 | Ortiz et al. |
| 2002/0177904 A1 | 11/2002 | Huxel et al. |
| 2003/0018358 A1 | 1/2003 | Saadat |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0130731 A1 | 7/2003 | Vidlund et al. |
| 2003/0167062 A1 | 9/2003 | Gambale et al. |
| 2003/0191528 A1 | 10/2003 | Quijano et al. |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2003/0233142 A1 | 12/2003 | Morales et al. |
| 2004/0024451 A1 | 2/2004 | Johnson et al. |
| 2004/0039442 A1 | 2/2004 | St. Goar et al. |
| 2004/0059413 A1 | 3/2004 | Argento |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133274 A1 | 7/2004 | Webler et al. |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0181287 A1 | 9/2004 | Gellman |
| 2004/0193191 A1 | 9/2004 | Starksen et al. |
| 2004/0236419 A1 | 11/2004 | Milo |
| 2004/0243227 A1 | 12/2004 | Starksen et al. |
| 2004/0249453 A1 | 12/2004 | Cartledge et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0016560 A1 | 1/2005 | Voughlohn |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0096740 A1 | 5/2005 | Langberg et al. |
| 2005/0107871 A1 | 5/2005 | Realyvasquez et al. |
| 2005/0125011 A1 | 6/2005 | Spence et al. |
| 2005/0137695 A1 | 6/2005 | Salahieh et al. |
| 2005/0171601 A1 | 8/2005 | Cosgrove |
| 2005/0177180 A1 | 8/2005 | Kaganov et al. |
| 2005/0177228 A1 | 8/2005 | Solem et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0288778 A1 | 12/2005 | Shaoulian et al. |
| 2005/0288781 A1 | 12/2005 | Moaddeb et al. |
| 2006/0004443 A1 | 1/2006 | Liddicoat et al. |
| 2006/0020326 A9 | 1/2006 | Bolduc et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0052868 A1 | 3/2006 | Mortier et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0129166 A1 | 6/2006 | Lavelle |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0241656 A1 | 10/2006 | Starksen et al. |
| 2006/0241745 A1* | 10/2006 | Lee et al. ............... 623/2.37 |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0016287 A1 | 1/2007 | Cartledge et al. |
| 2007/0016288 A1 | 1/2007 | Gurskis et al. |
| 2007/0027533 A1 | 2/2007 | Douk |
| 2007/0027536 A1 | 2/2007 | Mihaljevic et al. |
| 2007/0038221 A1 | 2/2007 | Fine et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0080188 A1 | 4/2007 | Spence et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0213582 A1 | 9/2007 | Zollinger et al. |
| 2007/0219558 A1 | 9/2007 | Deutsch |

(56) References Cited

U.S. PATENT DOCUMENTS

| | | |
|---|---|---|
| 2007/0239208 A1 | 10/2007 | Crawford |
| 2007/0244556 A1 | 10/2007 | Rfiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0282375 A1 | 12/2007 | Hindrichs et al. |
| 2007/0295172 A1 | 12/2007 | Swartz |
| 2008/0004697 A1 | 1/2008 | Lichtenstein et al. |
| 2008/0027483 A1 | 1/2008 | Cartledge et al. |
| 2008/0035160 A1 | 2/2008 | Woodson et al. |
| 2008/0039935 A1 | 2/2008 | Buch et al. |
| 2008/0058595 A1 | 3/2008 | Snoke et al. |
| 2008/0065204 A1 | 3/2008 | Macoviak et al. |
| 2008/0086203 A1 | 4/2008 | Roberts |
| 2008/0167714 A1 | 7/2008 | St. Goar et al. |
| 2008/0177382 A1 | 7/2008 | Hyde et al. |
| 2008/0195126 A1 | 8/2008 | Solem |
| 2008/0262609 A1 | 10/2008 | Gross et al. |
| 2008/0275469 A1 | 11/2008 | Fanton et al. |
| 2008/0281411 A1 | 11/2008 | Berreklouw |
| 2008/0288044 A1 | 11/2008 | Osborne |
| 2009/0043153 A1 | 2/2009 | Zollinger et al. |
| 2009/0054969 A1 | 2/2009 | Salahieh et al. |
| 2009/0076586 A1 | 3/2009 | Hauser et al. |
| 2009/0076600 A1 | 3/2009 | Quinn |
| 2009/0099650 A1 | 4/2009 | Bolduc et al. |
| 2009/0125102 A1 | 5/2009 | Cartledge et al. |
| 2009/0149872 A1 | 6/2009 | Gross et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0023117 A1 | 1/2010 | Yoganathan et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063586 A1 | 3/2010 | Hasenkam et al. |
| 2010/0076499 A1 | 3/2010 | McNamara et al. |
| 2010/0130992 A1 | 5/2010 | Machold et al. |
| 2010/0152845 A1 | 6/2010 | Bloom et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0174358 A1 | 7/2010 | Rabkin et al. |
| 2010/0179574 A1 | 7/2010 | Longoria et al. |
| 2010/0211166 A1 | 8/2010 | Miller et al. |
| 2010/0234935 A1 | 9/2010 | Bashiri et al. |
| 2010/0249915 A1 | 9/2010 | Zhang |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0324598 A1 | 12/2010 | Anderson |
| 2011/0011917 A1 | 1/2011 | Loulmet |
| 2011/0029066 A1 | 2/2011 | Gilad et al. |
| 2011/0066231 A1 | 3/2011 | Cartledge et al. |
| 2011/0082538 A1 | 4/2011 | Dahlgren et al. |
| 2011/0093002 A1 | 4/2011 | Rucker et al. |
| 2011/0106245 A1 | 5/2011 | Miller et al. |
| 2011/0106247 A1 | 5/2011 | Miller et al. |
| 2011/0118832 A1 | 5/2011 | Punjabi |
| 2011/0166649 A1 | 7/2011 | Gross et al. |
| 2011/0184510 A1 | 7/2011 | Maisano et al. |
| 2011/0190879 A1 | 8/2011 | Bobo et al. |
| 2011/0202130 A1 | 8/2011 | Cartledge et al. |
| 2011/0208283 A1 | 8/2011 | Rust |
| 2011/0224785 A1 | 9/2011 | Hacohen |
| 2011/0230961 A1 | 9/2011 | Langer et al. |
| 2011/0238088 A1 | 9/2011 | Bolduc et al. |
| 2011/0257633 A1 | 10/2011 | Cartledge et al. |
| 2011/0257728 A1 | 10/2011 | Kuehn |
| 2011/0282361 A1 | 11/2011 | Miller et al. |
| 2011/0288635 A1 | 11/2011 | Miller et al. |
| 2011/0301698 A1 | 12/2011 | Miller et al. |
| 2012/0022557 A1 | 1/2012 | Cabiri et al. |
| 2012/0078355 A1 | 3/2012 | Zipory et al. |
| 2012/0078359 A1 | 3/2012 | Li et al. |
| 2012/0095552 A1 | 4/2012 | Spence et al. |
| 2012/0123531 A1 | 5/2012 | Tsukashima et al. |
| 2012/0136436 A1 | 5/2012 | Cabiri et al. |
| 2012/0143323 A1 | 6/2012 | Hasenkam et al. |
| 2012/0150290 A1 | 6/2012 | Gabbay |
| 2012/0296419 A1 | 11/2012 | Richardson et al. |
| 2012/0323313 A1 | 12/2012 | Seguin |
| 2012/0330410 A1 | 12/2012 | Hammer et al. |
| 2012/0330411 A1 | 12/2012 | Gross et al. |
| 2013/0079873 A1 | 3/2013 | Migliazza et al. |
| 2013/0090724 A1 | 4/2013 | Subramanian et al. |
| 2013/0096672 A1 | 4/2013 | Reich et al. |
| 2013/0096673 A1 | 4/2013 | Hill et al. |
| 2013/0116780 A1 | 5/2013 | Miller et al. |
| 2013/0123910 A1 | 5/2013 | Cartledge et al. |
| 2013/0131792 A1 | 5/2013 | Miller et al. |
| 2013/0197632 A1 | 8/2013 | Kovach et al. |
| 2013/0204361 A1 | 8/2013 | Adams et al. |
| 2013/0226289 A1 | 8/2013 | Shaolian et al. |

FOREIGN PATENT DOCUMENTS

| | | |
|---|---|---|
| WO | 01/26586 | 4/2001 |
| WO | 02085251 A1 | 10/2002 |
| WO | 02085252 A1 | 10/2002 |
| WO | 03/047467 | 6/2003 |
| WO | 2004/103434 | 12/2004 |
| WO | 2005021063 A2 | 3/2005 |
| WO | 2005/046488 | 5/2005 |
| WO | 2006/012013 | 2/2006 |
| WO | 2006/012038 | 2/2006 |
| WO | 2006/086434 | 8/2006 |
| WO | 2006/097931 | 9/2006 |
| WO | 2006/105084 | 10/2006 |
| WO | 2006/116558 | 11/2006 |
| WO | 2007/011799 | 1/2007 |
| WO | 2007136783 A2 | 11/2007 |
| WO | 2008/068756 | 6/2008 |
| WO | 2010073246 A2 | 7/2010 |
| WO | 2011089601 A1 | 7/2011 |

OTHER PUBLICATIONS

O'Reilly S et al., "Heart valve surgery pushes the envelope", Medtech Insight 8(3): 73, 99-108, 2006.

Dieter RS, "Percutaneous valve repair: Update on mitral regurgitation and endovascular approaches to the mitral valve", Applications in imaging, Cardiac Interventions, Supported by an educational grant from Amersham Health pp. 11-14, 2003.

Swain CP et al., "An endoscopiacally deliverable tissue-transfixing device for securing biosensors in the gastrointestinal tract", Gastointestinal Endoscopy 40(6): 730-734, 1994.

U.S. Appl. No. 60/873,075, filed Dec. 5, 2006; pp. 1-23.

U.S. Appl. No. 60/902,146, filed Feb. 16, 2007; pp. 1-401.

U.S. Appl. No. 61/001,013, filed Oct. 29, 2007; pp. 1-97.

U.S. Appl. No. 12/689,693 Final Office Action dated Feb. 3, 2014.

ISR PCTIL1350860 dated Apr. 9, 2014.

Non-Final Office Action for U.S. Appl. No. 13/666,262, filed Nov. 1, 2012, Notification Date Dec. 16, 2013, 23 pages.

EP07849540 Search Reportt dtd Feb. 1, 2011.

Amendment, Terminal Disclaimer and Extension dated Jun. 27, 2012 from U.S. Appl. No. 12/548,991.

English Translation of JP Patent Application No. 2009-539871 OA dated Oct. 23, 2012.

IPR on Patentability PCTIL2010000358 dtd Nov. 9, 2011.

ISR PCT IL09 00593; Sep. 8, 2009.

ISR PCT IL09 01209; Jun. 10, 2010.

ISR PCT IL10 00357; Aug. 17, 2010 and Written Opinion.

(56) References Cited

OTHER PUBLICATIONS

ISR Dec. 29, 2010, later publication, PCTIL201000358.
OA dtd Jan. 23, 2013 from U.S. Appl. No. 12/692,061.
OA dtd Jan. 27, 2012 from U.S. Appl. No. 12/548,991.
OA dtd Feb. 12, 2013 from U.S. Appl. No. 12/926,673.
OA dtd Apr. 6, 2010 from U.S. Appl. No. 12/484,512.
OA dated Aug. 4, 2010 from U.S. Appl. No. 12/341,960.
OA dtd Nov. 14, 2011 from U.S. Appl. No. 12/608,316.
Tajik, AJ, et al., "Two-dimensional real-time ultrasonic imaging of the heart and great vessels. Technique, image orientation, structure identification, and validation." Mayo Clinic Proceedings, vol. 53, pp. 271-303 (1978). Abstract Only.
U.S. Appl. No. 61/132,295, filed Jun. 16, 2008.
Final Office Action, U.S. Appl. No. 14/027,934, dated Jun. 11, 2014.
ISR and Written Opinion_PCT/IL13/50860 dated Apr. 9, 2014.
Non-Final Office Action, U.S. Appl. No. 12/840,463, dated Jun. 4, 2014.
Non-Final Office Action, U.S. Appl. No. 13/167,492, dated Jun. 10, 2014.
Notice of Allowance, U.S. Appl. No. 13/666,262 dated Jun. 25, 2014.
CN OA 201080059948.4 dated Apr. 23, 2014.
Restriction Requirement, U.S. Appl. No. 13/319,030 dated Jun. 2, 2014.
Office Action dated Oct. 6, 2010, which issued during the prosecution of Applicant's U.S. Appl. No. 12/484,512.
ISR PCT IL2011 00064 dated May 19, 2011.

* cited by examiner

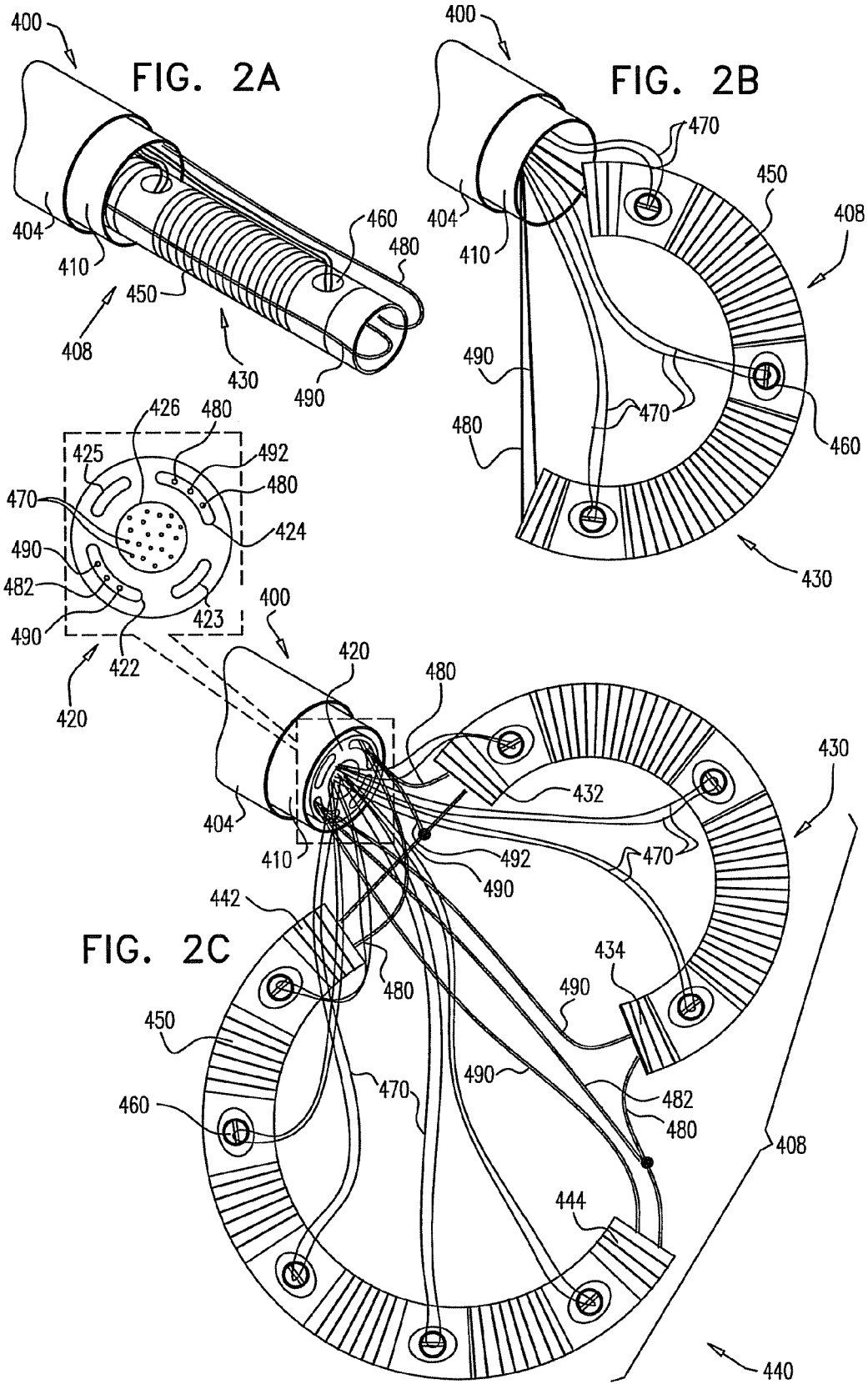

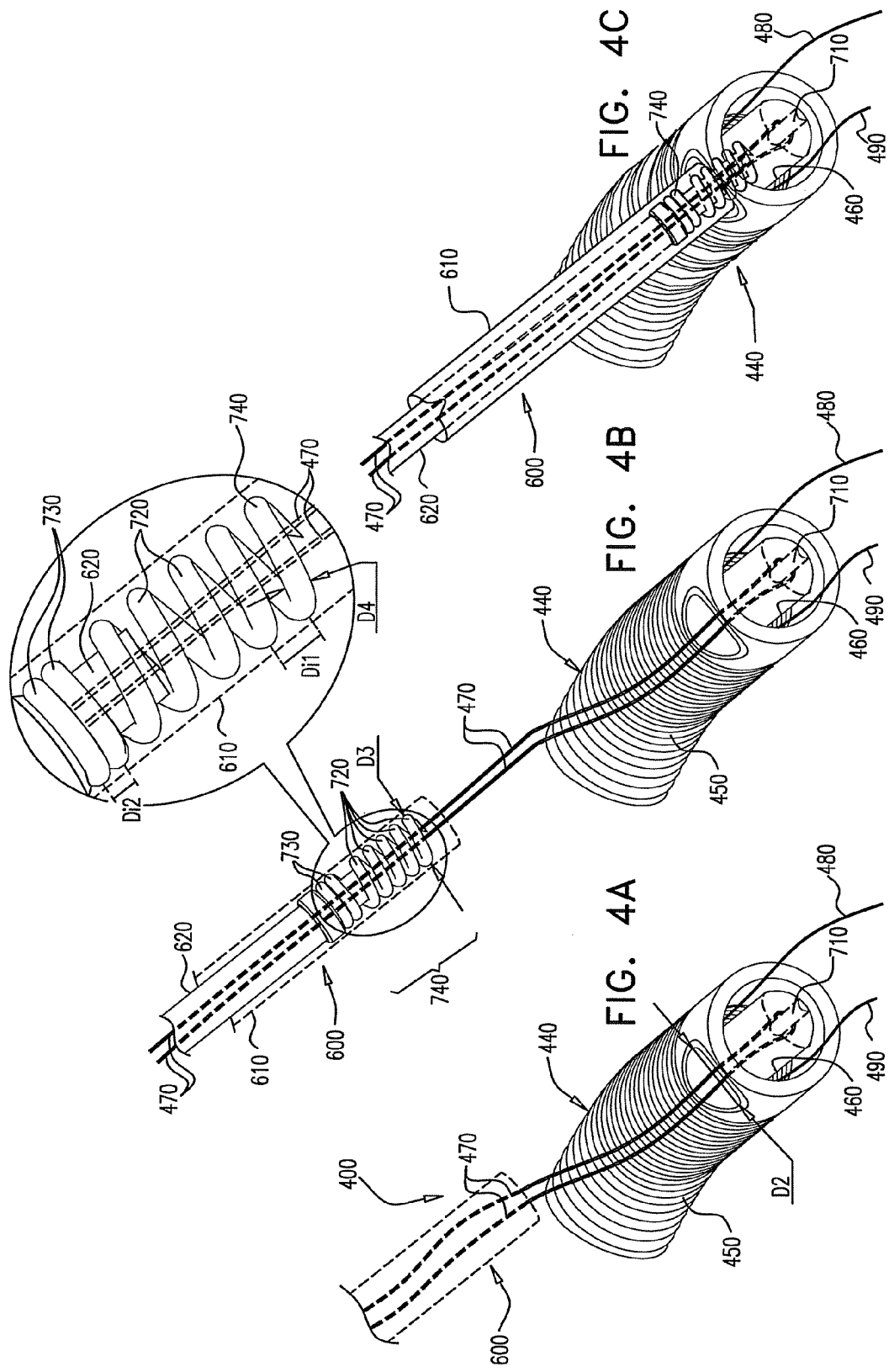

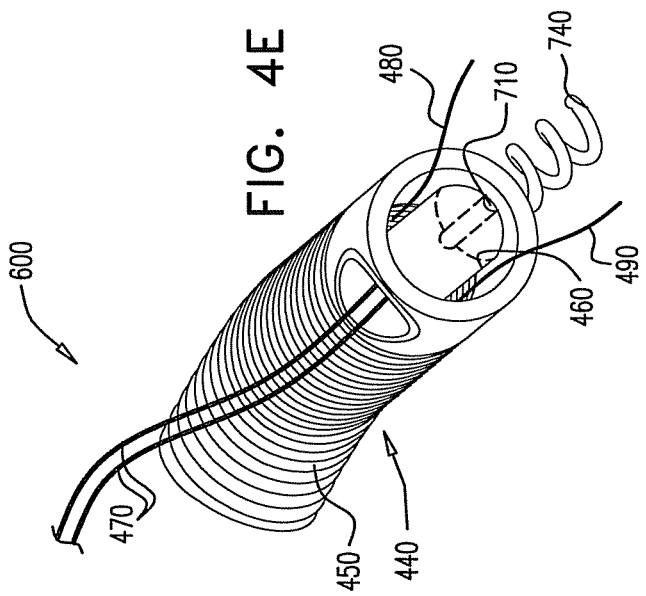
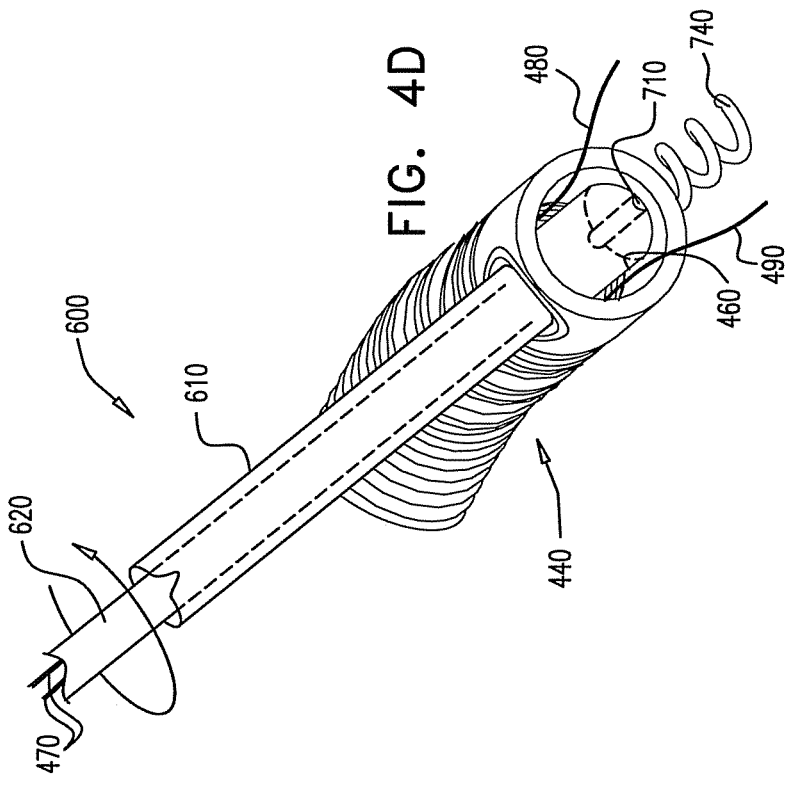

SEGMENTED RING PLACEMENT

CROSS-REFERENCES TO RELATED APPLICATIONS

This application is related to a PCT patent application to Gross et al., entitled, "Segmented ring placement," filed on even date herewith, and claims priority from:

(a) U.S. Provisional Patent Application 60/873,075 to Gross et al., entitled, "Mitral valve closure techniques," filed Dec. 5, 2006;

(b) U.S. Provisional Patent Application 60/902,146 to Gross et al., entitled, "Mitral valve closure techniques," filed on Feb. 16, 2007; and (c) a US provisional patent application to Gross et al., entitled, "Segmented ring placement," filed Oct. 29, 2007.

All of these applications are incorporated herein by reference.

FIELD OF THE INVENTION

The present invention relates in general to valve repair. More specifically, the present invention relates to percutaneous repair of a mitral valve of a patient.

BACKGROUND OF THE INVENTION

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Stretching of the leaflets of the valve and of the associated chordae tendineae prevents the valve leaflets from fully coapting when the valve is closed, causing the valve leaflets to prolapse into the left atrium. Mitral regurgitation of blood from the left ventricle into the left atrium results in increased total stroke volume and decreased cardiac output, and ultimate weakening of the left ventricle secondary to a volume overload and a pressure overload of the left atrium.

US Patent Application Publication 2005/0004668 to Aklog et al., which is incorporated herein by reference, describes implantable devices and methods for the repair of a defective cardiac valve. The implantable devices include an annuloplasty ring and a restraining and/or a remodeling structure or mechanism. The annuloplasty ring functions to reestablish the normal size and shape of the annulus bringing the leaflets in proximity to each other. A device having a remodeling structure further facilitates remodeling of the valve but allows the use of a flexible ring. The restraining structure functions to restrain the abnormal motion of at least a portion of the valve being repaired. The restraining and remodeling structures may include at least one strut across the interior of the circumference of the ring.

US Patent Application Publication 2005/0171601 to Cosgrove, which is incorporated herein by reference, describes an annuloplasty repair segment and template for heart valve annulus repair. The elongate flexible template may form a distal part of a holder that also has a proximal handle. Alternatively, the template may be releasably attached to a mandrel that slides within a delivery sheath, the template being released from the end of the sheath to enable manipulation by a surgeon. A tether connecting the template and mandrel may also be provided. The template may be elastic, temperature responsive, or multiple linked segments. The template may be aligned with the handle and form a two- or three-dimensional curve out of alignment with the handle such that the annuloplasty repair segment attached thereto conforms to the curve. The template may be actively or passively converted between its straight and curved positions. The combined holder and ring are suited for minimally-invasive surgeries in which the combination is delivered to an implantation site through a small access incision with or without a cannula, or through a catheter passed though the patient's vasculature.

U.S. Pat. No. 6,569,198 to Wilson et al., which is incorporated herein by reference, describes an elongated member that includes distal and proximal segments separated by an intermediate segment. The prosthetic device has at least one anchor control wire to anchor the device in the blood vessel and at least one length control wire. A second preferred embodiment is an elongated member that includes distal and proximal segments that are connected by a pivot or hinge joint. A control wire is anchored on the distal segment and pivotally moves the distal and proximal segments closer together. Rotation of the length control wire of the first embodiment or the control wire of the second embodiment reduces the circumference of the valve annulus.

U.S. Pat. No. 6,102,945 to Campbell, which is incorporated herein by reference, describes a support ring for a natural human heart valve, including a first ring portion having opposite terminal ends and a second ring portion having opposite terminal ends. An interconnector extends through and interconnects the first and second ring portions, to maintain the opposite terminal ends of the first ring portion adjacent the opposite terminal ends of the second ring portion, to form a segmented ring having a first and a second interface between the first and second ring portions. The first ring portion is of a greater length than the second ring portion. The ring portions are separable by severing the interconnector at the first and second interfaces, thus producing two variable size ring segments.

U.S. Pat. No. 6,217,610 to Carpentier et al., which is incorporated herein by reference, describes an expandable annuloplasty ring which may either expand spontaneously, in situ, as the patient grows or be expanded by surgical intervention by balloon dilatation. The distensible annuloplasty ring may be usable in pediatric patients whose growth, subsequent to surgical implantation of the ring, will necessitate subsequent enlargement of the ring to accommodate growth of the annulus. The ring may include relatively expandable segments to enable the enlargement thereof. The ring segments may include engaging teeth which cooperate with notches or slots formed in the tubes to provide some resistance to ring distention, while preventing collapse of the ring in the opposite direction. The teeth may be of different sizes or shapes to regulate the amount of force needed to expand the ring at different stages of the patient's growth. Alternatively, the adjustable ring includes a solid core of non-elastic material which plastically retains its shape upon natural expansion of the annulus, or after surgical expansion. In one embodiment, segments are coupled together with a discontinuity around the ring periphery. Pivot regions are provided between adjacent segments that, along with the discontinuity, enable the ring to expand upon annulus growth. The discontinuity may be positioned along the anterior side of the ring or around the posterior side. A further version makes use of telescoped segments with no discontinuity. The segments are coupled together with tubular sheaths, and expand without decoupling. A fabric covering may be omitted.

US Patent Application Publication 2003/0018358 to Saadat, which is incorporated herein by reference, describes techniques for thermally and/or mechanically treating tissue, such as valvular structures, to reconfigure or shrink the tissue in a controlled manner. Mechanical clips are implanted over the leaflets of a valve, e.g., in the heart, either alone or after thermal treatment to cause the valve to close more tightly. The clips are delivered by a catheter and may be configured to traverse directly over the valve itself or to lie partially over the periphery of the valve to prevent obstruction of the valve channel. Alternatively, individual anchors with a tensioning element, like a suture, are described as being useful for approximating the valves towards each other.

US Patent Application Publications 2004/0260393 to Rahdert et al. and 2004/0127982 to Machold et al., which are incorporated herein by reference, describe techniques using an implant that is sized and configured to attach in, on, or near the annulus of a dysfunctional heart valve. In use, the implant extends either across the minor axis of the annulus, or across the major axis of the annulus, or both. The implant is described as restoring to the heart valve annulus and leaflets a more functional anatomic shape and tension. The more functional anatomic shape and tension are conducive to coaptation of the leaflets, which, in turn, reduces retrograde flow or regurgitation. In some embodiments, the implant is configured to rest at or near a heart valve annulus and apply a direct mechanical force along the minor axis of the annulus to inwardly displace tissue toward the center of the annulus. For some applications, the implant is configured to extend significantly above the plane of the valve, while for other applications, the implant is configured to extend a short distance above the plane of the valve.

PCT Publication WO 01/26586 to Seguin, which is incorporated herein by reference, describes a device comprising: an implant with an elongated deformable structure, such that the implant can adopt an elongated shape to be inserted into the patient's body through a passage of reduced diameter and a curved shape adapted to perform annuloplasty; and a tubular instrument for receiving at least partly said implant therein, having a rigidity such that it enables the implant to be inserted in the patient's body through said passage; said instrument comprises an orifice at its distal end, providing access to the implant, means for locking the implant in rotation relative thereto, means for maintaining the implant relative thereto, and means for locating its angular orientation inside the patient's body. The device is described as being designed for use in the reconstruction of cardiac valves.

U.S. Pat. No. 5,593,424 to Northrup III, which is incorporated herein by reference, describes an apparatus and method for reducing the circumference of a vascular structure comprising the steps of providing a plurality of sutures and a plurality of discrete suture support segments of a biocompatible, inert material, each suture support segment having at least two suture holes spaced a predetermined distance (D) apart; individually suturing each discrete suture support segment to the vascular structure with one of the plurality of sutures by effecting a horizontal mattress (U-shaped) suture along the vascular structure through a length of tissue of the vascular structure such that the length (D') of tissue sutured is greater than distance (D); and tightening and tying off the suture, whereby each sutured suture support segment creates an imbrication in the vascular structure, thereby reducing the circumference thereof. A biocompatible, inert stabilizing material is described as being optionally affixed over the suture support segments and the vascular structure prior to tying off the suture to stabilize the interval between the suture support segments and eliminate direct exposure of the segmented apparatus to blood.

U.S. Pat. No. 3,656,185 to Carpentier, which is incorporated herein by reference, describes a cardiac valvular prosthesis, e.g., for the mitral valve, consisting solely of an annular or part-annular member adapted to fit against the base of the cusps of a human heart valve, and suture means for securing the member in place. The prosthesis cooperates with the natural valve cusps of the patient to form the valve.

The following patents and patent applications, which are incorporated herein by reference, may be of interest:

PCT Publication WO 06/105084 to Cartledge et al.
PCT Publication WO 03/047467 to Cosgrove et al.
PCT Publication WO 04/103434 to Martin et al.
PCT Publication WO 05/046488 to Douk et al.
PCT Publication WO 06/012013 to Rhee et al.
PCT Publication WO 06/012038 to Shaoulian et al.
PCT Publication WO 06/086434 to Powell et al.
PCT Publication WO 06/097931 to Gross et al.
PCT Publication WO 07/011,799 to Navia et al.
U.S. Pat. No. 5,306,296 to Wright et al.
U.S. Pat. No. 5,855,614 to Stevens et al.
U.S. Pat. No. 6,074,401 to Gardiner et al.
U.S. Pat. No. 6,619,291 to Hlavka et al.
U.S. Pat. No. 6,626,899 to Houser et al.
U.S. Pat. No. 6,629,534, PCT Publication WO 06/116558 and US Patent Application Publication 2004/0039442 to St. Goar et al.
U.S. Pat. No. 6,752,813 to Golfarb et al.
U.S. Pat. No. 6,764,510 to Vidlund et al.
U.S. Pat. No. 6,918,917 to Nguyen et al.
U.S. Pat. No. 6,926,730 to Nguyen et al.
U.S. Pat. No. 6,986,775 to Morales et al.
U.S. Pat. No. 7,004,176 to Lau
U.S. Pat. No. 7,101,395 to Tremulin et al.
U.S. Pat. No. 7,150,737 to Purdy et al.
U.S. Pat. Nos. 7,172,625 and 7,172,625 to Shu et al.
U.S. Pat. No. 7,175,660 to Cartledge et al.
US Patent Application Publication 2003/0050693 to Quijano et al.
US Patent Application Publication 2003/0078465 to Pai et al.
US Patent Application Publication 2003/0191528 and U.S. Pat. No. 6,805,711 to Quijano et al.
US Patent Application Publication 2003/0199974 to Lee et al.
US Patent Application Publication 2004/0127983 to Mortier et al.
US Patent Application Publication 2004/0148021 to Cartledge et al.
US Patent Application Publication 2004/0193191 to Starksen et al.
US Patent Application Publication 2004/0236419 to Milo
US Patent Application Publication 2004/0243227 to Starksen et al.
US Patent Application Publication 2004/0260394 to Douk et al.
US Patent Application Publication 2005/0055038 to Kelleher et al.
US Patent Application Publication 2005/0096740 to Langberg et al.
US Patent Application Publication 2005/0222678 to Lashinslci et al.
US Patent Application Publication 2005/0288778 to Shaoulian et al.
US Patent Application Publication 2005/0288781 to Moaddeb et al.
US Patent Application Publication 2006/0195134 to Crittenden
US Patent Application Publication 2006/0282161 to Huynh et al.
US Patent Application Publication 2006-0247763 to Slater US Patent Application Publication 2007/0080188 to Spence et al.

US Patent Application Publications 2004/0148019 and 2004/0148020 to Vidlund et al.

US Patent Application Publications 2005/0010287 and 2004/0138745 to Macoviak et al.

The following articles, which are incorporated herein by reference, may be of interest:

O'Reilly S et al., "Heart valve surgery pushes the envelope," Medtech Insight 8(3): 73, 99-108 (2006)

Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003)

Swain C P et al., "An endoscopically deliverable tissue-transfixing device for securing biosensors in the gastrointestinal tract," Gastrointestinal Endoscopy 40(6): 730-734 (1994)

Odell J A et al., "Early Results of a Simplified Method of Mitral Valve Annuloplasty," Circulation 92:150-154 (1995)

SUMMARY OF THE INVENTION

In some embodiments of the present invention, a system and minimally-invasive surgical methods are provided for repair of a dilated mitral valve of a patient. An annuloplasty structure, e.g., at least one segment of an annuloplasty ring, is transcatheterally advanced to an atrial surface of an annulus of the mitral valve, using a percutaneous approach. Typically, the annuloplasty structure comprises at least two discrete hollow ring segments which are each anchored at respective positions along the annulus circumference of the mitral valve. In embodiments in which two segments are used, the two segments are typically coupled together by two control wires, e.g., nitinol wires, which are configured for sliding motion through the segments. These wires function as drawstrings to pull the segments into proper orientation once the segments have been anchored to the annulus.

In some embodiments, the segments comprise accordion-like compressible structures which facilitate proper cinching of the annulus when the segments are drawn together. The accordion-like structures, when compressed, enable portions of the segments to independently conform to the configuration of the annulus of the mitral valve of a given patient. In embodiments in which the segments are shaped to define a coil, the coil is configured to be compressed.

Typically, the first of the two segments is sized such that it corresponds with the size of the base of the posterolateral leaflet at the annulus. Similarly, the second segment is designated to be anchored to the annulus at the base of the anteromedial leaflet, and thus is sized in accordance therewith. Such positioning of the segments at the base of respective leaflets of the mitral valve facilitates control of the leaflet corresponding to the respective segment. Additionally, the junctions between the two segments of the annuloplasty ring are adjacent to and mimic the physiological commissures of both leaflets of the mitral valve.

Typically, the annuloplasty structure comprises a flexible, biocompatible material, e.g., nitinol, PTFE (Polytetrafluoroethylene), stainless steel, platinum iridium, titanium, or silicone. In some embodiments, the annuloplasty structure is shaped to define a coil. For some applications, the coil is shaped to define a stent-like net configuration.

Prior to the transcatheter advancement of the system, at least one flexible longitudinal guide member is reversibly coupled at least in part to the annuloplasty structure. In some embodiments, the guide member comprises an anchoring structure at a distal tip thereof. In such an embodiment, the anchoring structure is screwed into the annulus upon rotating a proximal end of the guide member.

The ring segments are typically advanced toward the left atrium of the patient in a generally straight configuration within the catheter that advances them (i.e., the ring segments are not curved within the catheter), the straight configuration defining a respective longitudinal axis of each of the first and second segments. In an embodiment, the two ring segments are shaped to provide a plurality of channels oriented substantially perpendicularly with respect to the longitudinal axis of the segments. The channels are configured for the passage of the anchoring structure therethrough. A bar is disposed within each channel. For example, the bar may be disposed at the base of each channel, i.e., the portion of the channel designated to align with and contact the annulus. Prior to the transcatheter advancement of the system, a flexible longitudinal guide wire is coupled to, e.g., looped around, each bar.

Once the annuloplasty segments have been deployed within the left atrium of the patient and positioned upon the annulus of the mitral valve, anchoring structures are sequentially advanced along respective guide wires, through the channels, and are subsequently implanted within the annulus in order to anchor the segments to the annulus. The control wires are then replaced by a tensile suture. Using real-time monitoring, tactile feedback and optionally in combination with fluoroscopic imaging, the suture is then pulled. Consequently, the leaflets are drawn toward one another in accordance with the level of dilation of the preoperative mitral valve. Thus, generally the normal structural configuration is returned to the leaflets, effecting a reduction in mitral valve prolapse and regurgitation.

In some embodiments of the present invention, the system comprises a multilumen catheter shaped to provide a primary lumen and a secondary lumen. Typically, the multilumen catheter is configured to advance the segments through an advancement catheter and into the left atrium. In some embodiments, the multilumen catheter is disposed proximally to the ring segments and is configured to push the segments through the advancement catheter. For some applications, the annuloplasty ring segments are advanced through the primary lumen of the multilumen catheter.

Typically, the multilumen catheter, the two ring segments, the control wires, and the plurality of guide wires coupled thereto, are preloaded into a catheter prior to the percutaneous advancement of the catheter into the left atrium of the patient.

There is therefore provided, in accordance with an embodiment of the present invention, apparatus for repairing a valve of a body of a patient, the valve including an annulus and at least first and second leaflets, including:

at least a first discrete segment and a second discrete segment of an annuloplasty structure, each segment being shaped to provide a respective lateral wall, each lateral wall being shaped to define at least one lumen of the respective segment; and at least a first and a second control wire, each control wire configured for sliding advancement through both the first and second segments:

the first control wire is configured to control a relative disposition of a first end of the first segment and a first end of the second segment, and the second control wire is configured to control a relative disposition of a second end of the first segment and a second end of the second segment.

In an embodiment, the first and second segments are configured for transcatheter advancement into a left atrium of a patient.

In an embodiment, the first and second segments are configured for simultaneous advancement toward a left atrium of a patient.

In an embodiment, for each lateral wall of each segment, the lateral wall has a first and a second portion, and the segment is shaped to provide a channel extending from the first portion to the second portion.

In an embodiment, the apparatus includes a bar configured to be disposed within the channel.

In an embodiment, the bar is disposed within the channel substantially perpendicular to an axis of the channel.

In an embodiment, the apparatus includes a flexible longitudinal guide member configured to be removably coupled to the bar.

In an embodiment, the apparatus includes an anchoring structure, and while the guide member is disposed within the body of the patient, the anchoring structure is configured to be advanced via the guide member, through the channel, and subsequently anchored to the annulus of the patient.

In an embodiment, the anchoring structure includes a pointed distal tip.

In an embodiment, while the guide member is disposed within the body of the patient, the anchoring structure is configured to be advanced along the guide member from a site outside the body of the patient.

In an embodiment, while the guide member is disposed within the body of the patient, the guide member is configured to be decoupled from the bar subsequent to the anchoring of the anchoring structure to the annulus.

In an embodiment, the anchoring structure includes a helical element at a distal end thereof, the helical element shaped to provide a proximal end of the helical element and a distal end of the helical element.

In an embodiment, the apparatus includes an advancement tube having a distal tip thereof, at least a portion of the proximal end of the helical element is configured to be coupled to the distal tip of the advancement tube.

In an embodiment, the helical element is shaped to define a first number of proximal rotational subunits and a second number of distal rotational subunits, and the proximal rotational subunits are wrapped around the distal tip of the advancement tube.

In an embodiment, the proximal rotational subunits are coupled to the distal tip of the advancement tube by a first frictional force.

In an embodiment, the second number is greater than the first number.

In an embodiment, the advancement tube is configured to be rotated and, in response to the rotation, the distal rotational subunits are configured to be implanted within the annulus of the patient.

In an embodiment, at least a portion of the distal tip is shaped to define a protrusion disposed adjacent to the proximal end of the helical element, the protrusion being configured to apply a circumferentially-directed force to the proximal end of the helical element as the advancement tube is rotated.

In an embodiment, during the rotation of the advancement tube:
the proximal rotational subunits are configured to slide distally along the distal tip of the advancement tube, and
in response to the sliding, a portion of the first number of proximal rotational subunits remains wrapped around the distal tip of the advancement tube.

In an embodiment, a number of proximal rotational subunits in the portion is less than the first number of proximal rotational subunits.

In an embodiment, the portion of the proximal rotational subunits is coupled to the distal tip of the advancement tube by a second frictional force, the second frictional force being weaker than the first frictional force.

In an embodiment, the second frictional force being weaker than the first frictional force facilitates decoupling of the distal tip of the advancement tube from the helical element.

In an embodiment:
the helical element is shaped to define at least two adjacent distal rotational subunits and at least two adjacent proximal rotational subunits, and
a distance between the two adjacent distal rotational subunits is greater than a distance between the two adjacent proximal rotational subunits.

In an embodiment, the distance between the distal rotational subunits enables the distal rotational subunits to be corkscrewed around the bar and subsequently into the annulus of the patient.

In an embodiment, the distance between the proximal rotational subunits restricts the proximal rotational subunits from being corkscrewed around the bar and into the annulus of the patient.

In an embodiment, the first and second segments are configured to be advanced toward a left atrium of the patient in a generally straight configuration and subsequently are made to assume a curved configuration.

In an embodiment, the first and second control wires are configured to pull the first and second segments into curved configurations.

In an embodiment, the first and second segments include a shape-memory alloy, the alloy being configured to assume a curved configuration once the segments have been advanced into the left atrium of the patient.

In an embodiment, the apparatus includes at least first and second flexible longitudinal guide members, the first and second guide members configured to be removably coupled to the first and second segments, respectively, each guide member being configured to facilitate anchoring of the respective segment to the annulus of the patient.

In an embodiment, the apparatus includes respective at least first and second anchoring structures, the first and second anchoring structures configured to be disposed at respective distal ends of the first and second guide members, respectively, the anchoring structures being configured to be screwed into the annulus of the patient in response to a rotational force applied to a respective proximal end of the respective guide members.

In an embodiment, each of the anchoring structures includes a pointed distal tip.

In an embodiment, the first and second control wires are configured to control a relative disposition of the first and second segments.

In an embodiment, the first and second control wires are configured to separate the first and second segments.

In an embodiment, the first and second control wires are configured to facilitate positioning of the first and second segments along the annulus.

In an embodiment, the first and second segments are configured to be advanced toward a left atrium of the patient in a generally straight configuration thereof, and the first and second control wires are configured to pull the first and second segments into a curved configuration.

In an embodiment, the first and second segments are configured to be advanced toward an atrium of a heart of the patient in a generally straight configuration, the straight configuration defining a longitudinal axis of the respective first and second segments, at least a portion of the first and second segments is shaped to define one or more compressible units, and the compressible units are configured to be compressed in parallel with the longitudinal axis of the respective segments.

In an embodiment, the compressible units are configured to be compressed in response to an application of a pulling force to the first and second control wires.

In an embodiment, the first control wire is configured to compress the first segment at least in part in response to an application of a pulling force to at least a portion of the first control wire, and the second control wire is configured to compress the second segment at least in part in response to an application of a pulling force to at least a portion of the second control wire.

In an embodiment, the apparatus includes first and second adjustment wires, coupled to the first and second control wires, respectively, the first adjustment wire is coupled to the first control wire at a first junction between the first and second segments, and the second adjustment wire is coupled to the second control wire at a second junction between the first and second segments.

In an embodiment, the adjustment wires are configured to facilitate aligning of the first and second segments with the annulus by separating the segments.

In an embodiment, the adjustment wires are configured to facilitate aligning of the first and second segments with the annulus by elevating portions of the first and second segments.

There is further provided, in accordance with an embodiment of the present invention apparatus for repairing a valve of a body of a patient, the valve including an annulus and at least first and second leaflets, including:

an annuloplasty structure,
shaped to provide one or more channels, each channel extending from a respective first portion of a lateral wall of the annuloplasty structure to a respective second portion of the lateral wall of the annuloplasty structure, and
including one or more bars, each bar configured to be disposed within a respective one of the channels; and
one or more flexible longitudinal guide members, each guide member configured to be removably coupled to a respective one of the bars.

In an embodiment, each guide member is removably coupled to the respective bar by being looped around the respective bar.

In an embodiment, the annuloplasty structure includes an annuloplasty ring.

In an embodiment, the annuloplasty structure includes a partial annuloplasty ring.

In an embodiment, the structure and the one or more guide members are configured to be transcatheterally advanced into a left atrium of the patient.

In an embodiment, the structure and the one or more guide members are configured to be simultaneously advanced toward a left atrium of the patient.

In an embodiment, the annuloplasty structure includes two or more segments of an annuloplasty ring.

In an embodiment, each bar is disposed within a respective one of the channels substantially perpendicular to an axis of the channel.

In an embodiment, the structure includes a shape-memory alloy.

In an embodiment, the structure is configured to be advanced toward a left atrium of the patient in a generally straight configuration and subsequently to be made to assume a curved configuration.

In an embodiment, the apparatus includes at least one control wire, and the control wire is configured to pull the structure into the curved configuration.

In an embodiment, the structure includes a shape-memory alloy, the alloy being configured to assume a curved configuration once the structure has been advanced into the left atrium of the patient.

In an embodiment, the apparatus includes at least one control wire in communication with the structure configured to adjust a disposition of the structure.

In an embodiment, the lateral wall of the annuloplasty structure is shaped to define at least one lumen of the structure.

In an embodiment, the at least one control wire is configured for sliding advancement through the at least one lumen, and to control from within the lumen a conformation of the structure.

In an embodiment, the structure is configured to be advanced toward a left atrium of the patient in a generally straight configuration, the straight configuration defining a longitudinal axis thereof, at least a portion of the structure is shaped to define one or more compressible units, and the compressible units are configured to be compressed in parallel with the longitudinal axis.

In an embodiment, the compressible units are configured to be compressed in response to an application of a pulling force to the at least one control wire.

In an embodiment, the structure includes a first and a second segment, the first and second segments each shaped to provide a respective lateral wall, each lateral wall being shaped to define at least one respective lumen of the respective segment.

In an embodiment, the apparatus includes at least one adjustment wire coupled to the at least one control wire, and the at least one adjustment wire is configured to be coupled to the at least one control wire at a junction between the first and second segments.

In an embodiment, the at least one adjustment wire is configured to facilitate aligning of the first and second segments with the annulus by separating the segments.

In an embodiment, the at least one adjustment wire is configured to facilitate aligning of the first and second segments with the annulus by elevating portions of at least one of the segments.

In an embodiment, the control wire is configured for sliding advancement through the at least one lumen of each of the first and second segments.

In an embodiment, the at least one control wire includes a first and a second control wire.

In an embodiment:

the first and second segments are each shaped to provide respective first and second lumens, and the first control wire is configured for sliding advancement through each of the first lumens, and the second control wire is configured for sliding advancement through each of the second lumens.

In an embodiment, the first and second control wires are configured to control a relative disposition of the first and second segments.

In an embodiment, the first and second control wires are configured to separate portions of the first and second segments.

In an embodiment, the first and second control wires are configured to facilitate positioning of the first and second segments along the annulus.

In an embodiment, the first and second segments are configured to be advanced toward a left atrium of the patient in a generally straight configuration thereof, and the first and second control wires are configured to pull the first and second segments into a curved configuration.

In an embodiment, the first and second segments are configured to be advanced toward a left atrium of the patient in a generally straight configuration, the straight configuration defining a longitudinal axis of the respective first and second segments, at least a portion of each of the first and second segments is shaped to define one or more compressible units, and the compressible units are configured to be compressed in parallel with the longitudinal axis of the respective segments.

In an embodiment, the compressible units are configured to be compressed in response to an application of a pulling force to the first and second control wires.

In an embodiment:

the first control wire is configured to compress the first segment at least in part in response to an application of a pulling force to at least a portion of the first control wire, and the second control wire is configured to compress the second segment at least in part in response to an application of a pulling force to at least a portion of the second control wire.

In an embodiment, the apparatus includes one or more anchoring structures, each anchoring structure configured to be advanced through a respective one of the channels and subsequently anchored to the annulus of the patient.

In an embodiment, the anchoring structure is shaped to define a pointed distal tip.

In an embodiment, while the guide member is disposed within the body of the patient, each anchoring structure is configured to be advanced along a respective one of the guide members from a site outside the body of the patient.

In an embodiment, the guide member is configured to be decoupled from the bar subsequent to the anchoring of the anchoring structure to the annulus.

In an embodiment, each of the anchoring structures includes a helical element at a distal end thereof.

In an embodiment:

the helical element is shaped to define at least two adjacent distal rotational subunits and at least two adjacent proximal rotational subunits, and a distance between the two adjacent distal rotational subunits is greater than a distance between the two adjacent proximal rotational subunits.

In an embodiment, the distance between the distal rotational subunits enables the distal rotational subunits to be corkscrewed around the bar and subsequently into the annulus of the patient.

In an embodiment, the distance between the proximal rotational subunits restricts the proximal rotational subunits from being corkscrewed fully around the bar and into the annulus of the patient.

There is yet further provided, in accordance with an embodiment of the present invention apparatus for repairing a valve of a body of a patient, the valve including an annulus and at least first and second leaflets, including:

an annuloplasty structure including a bar; and an anchoring structure including a helical element, the helical element shaped to define at least two adjacent distal rotational subunits and at least two adjacent proximal rotational subunits, a distance between the two adjacent distal rotational subunits is greater than a distance between the two adjacent proximal rotational subunits, and:

the distance between the distal rotational subunits enables the distal rotational subunits to be corkscrewed around the bar and subsequently into tissue of a patient, and the distance between the proximal rotational subunits restricts the proximal rotational subunits from being corkscrewed into tissue of the patient.

In an embodiment, the annuloplasty structure includes an annuloplasty ring.

In an embodiment, the annuloplasty structure includes a partial annuloplasty ring.

In an embodiment, the annuloplasty structure includes two or more segments of an annuloplasty ring.

In an embodiment, the apparatus includes a flexible longitudinal guide member reversibly coupled to the structure, and configured to facilitate anchoring of the annuloplasty structure to the annulus of the patient.

In an embodiment, the annuloplasty structure is shaped to provide a lateral wall having at least first and second portions, and shaped to provide at least one channel, the at least one channel extends from the first portion of the lateral wall of the structure to the second portion of the lateral wall of the structure, the bar is disposed within the at least one channel substantially perpendicular to an axis of the channel, and the guide member is reversibly coupled to the bar.

In an embodiment, the anchoring structure is disposed at a distal end of the guide member.

In an embodiment, the anchoring structure is configured to be screwed into the annulus in response to a rotational force applied to a proximal end of the guide member.

In an embodiment, the apparatus includes a hollow tube configured to be reversibly coupled to the helical element, and to push the anchoring structure toward the annuloplasty structure.

In an embodiment, the hollow tube is configured to be advanced around the guide member while the guide member is disposed within the body of the patient.

In an embodiment, the helical element is disposed around the hollow tube, the hollow tube is configured to be rotated at a proximal portion thereof, and the anchoring structure is corkscrewed into the annulus of the patient in response to the rotation of the tube.

In an embodiment, a diameter of the bar is greater than the distance between the proximal rotational subunits, and during an attempt to corkscrew the proximal rotational subunits therearound:

the bar restricts the proximal rotational subunits from being corkscrewed into tissue of the patient by applying a counterforce to a torque applied by the rotation of the tube, and the proximal rotational subunits are configured to expand radially in response to the counterforce applied by the bar.

In an embodiment, the helical element is configured to be detached from the hollow tube in response to the radial expansion of the proximal rotational subunits.

There is additionally provided, in accordance with an embodiment of the present invention, a method for performing an annuloplasty on a valve of a body of a patient the valve including an annulus and at least first and second leaflets, including:

deploying an annuloplasty structure in an atrium of a heart of the patient, the structure including one or more bars and one or more respective flexible longitudinal guide members, each guide member reversibly coupled to a respective one of the bars;

positioning the annuloplasty structure along the annulus of the valve of the patient;

advancing one or more respective anchoring structures, each anchoring structure each anchoring structure being passed along a respective one of the flexible longitudinal guide members while the one or more guide members are disposed within the body of the patient;

advancing at least a portion of each anchoring structure beyond the respective bar and into tissue of the patient; and decoupling each guide member from the respective bar.

In an embodiment, deploying the annuloplasty structure includes placing the annuloplasty structure in the atrium during an open heart procedure.

In an embodiment, deploying the annuloplasty structure includes deploying at least one segment of an annuloplasty ring.

In an embodiment, deploying the annuloplasty structure includes deploying an annuloplasty ring.

In an embodiment, deploying the annuloplasty structure includes deploying a partial annuloplasty ring.

In an embodiment, the method includes advancing the annuloplasty structure to the atrium transcatheterally.

In an embodiment, the method includes performing, during a single transcatheter advancement, the steps of: (a) deploying the annuloplasty structure, (b) positioning the annuloplasty structure, (c) advancing the one or more respective anchoring structures, (d) advancing the at least a portion of each anchoring structure, and (e) decoupling each guide member.

In an embodiment, positioning the annuloplasty structure includes adjusting a configuration of the annuloplasty structure with respect to a configuration of the annulus of the patient.

In an embodiment, the annuloplasty structure is generally ring-shaped following the deployment, thereby defining a radius characteristic thereof, and adjusting the configuration of the structure includes reducing the radius by compressing at least a portion of the structure.

In an embodiment, compressing includes applying a pulling force to a control wire disposed within a lumen of the structure.

In an embodiment, deploying the structure includes deploying two segments of the annuloplasty ring.

In an embodiment, the method includes drawing together the first and second segments.

In an embodiment, positioning the structure along the annulus of the patient includes positioning the first and second segments along the annulus.

In an embodiment, positioning the first and second segments includes positioning the first segment on the annulus along a junction between a base of a first leaflet and the annulus, and positioning the second segment on the annulus along a junction between a base of a second leaflet and the annulus.

In an embodiment, positioning the first and second segments includes adjusting a relative disposition of the first and second segments with respect to a configuration of the annulus of the patient.

In an embodiment, adjusting the disposition of the first and second segments includes elevating at least a portion of the first segment and at least a portion of the second segment.

In an embodiment, adjusting the first and second segments includes adjusting the first segment independently of the adjusting of the second segment.

In an embodiment, the annuloplasty structure is configured to assume a generally straight configuration following the deployment, the straight configuration defining a longitudinal axis of the structure, and adjusting the disposition of the first and second segments includes adjusting a disposition of the first and second segments by compressing in parallel with the longitudinal axis of the structure at least a portion of the first segment and at least a portion of the second segment.

In an embodiment, compressing includes applying a pulling force to at least one control wire disposed within a lumen of each of the first and second segments.

There is also provided, in accordance with an embodiment of the present invention, apparatus for repairing a valve of a body of a patient, the valve including an annulus and at least first and second leaflets, including:

an annuloplasty structure; and
a flexible longitudinal guide member removably coupled to the structure:
the guide member is configured to facilitate anchoring of the annuloplasty structure to the annulus of the patient, and
the guide member is configured to be advanced toward the annulus simultaneously with the annuloplasty structure.

In an embodiment, the annuloplasty structure includes an annuloplasty ring.

In an embodiment, the annuloplasty structure includes a partial annuloplasty ring.

In an embodiment, the annuloplasty structure includes at lest first and second segments of an annuloplasty ring.

In an embodiment, the apparatus includes an anchoring structure configured to anchor the structure to the annulus via the guide member.

In an embodiment. the anchoring structure includes a pointed distal tip.

In an embodiment, of the anchoring structure is disposed at a distal end of the guide member, and is configured to be screwed into the annulus in response to a rotational force applied to a proximal end of the guide member.

In an embodiment, the annuloplasty structure is shaped to define a lateral wall having first and second portions, and to provide a channel extending from the first portion of the lateral wall to the second portion of the lateral wall of the structure.

In an embodiment, the anchoring structure is configured to be advanced through the channel and subsequently anchored to the annulus of the patient while the one or more guide members are disposed within the body of the patient.

In an embodiment, the apparatus includes a bar configured to be disposed within the channel.

In an embodiment, the bar is disposed within the channel substantially perpendicular to an axis of the channel.

In an embodiment, the guide member is configured to be removably coupled to the bar.

In an embodiment, the anchoring structure is configured to be advanced along the guide member from a site outside the body of the patient while the guide member is disposed within the body of the patient.

In an embodiment, the guide member is configured to be decoupled from the bar subsequent to the anchoring of the anchoring structure to the annulus.

In an embodiment, the anchoring structure includes a helical element at a distal end thereof, the helical element being configured to be corkscrewed at least in part into the annulus of the patient.

In an embodiment, the helical element is shaped to define at least two adjacent distal rotational subunits and at least two adjacent proximal rotational subunits, and a distance between the two adjacent distal rotational subunits is greater than a distance between the two adjacent proximal rotational subunits.

In an embodiment, the distance between the distal rotational subunits enables the distal rotational subunits to be corkscrewed around the bar and subsequently into the annulus of the patient.

In an embodiment, the distance between the proximal rotational subunits restricts the proximal rotational subunits from being corkscrewed around the bar and into the annulus of the patient.

The present invention will be more fully understood from the following detailed description of embodiments thereof, taken together with the drawings, in which:

BRIEF DESCRIPTION OF THE DRAWINGS

FIGS. 2A-F are schematic illustrations of the deployment of two annuloplasty ring segments of the system toward the annulus of the patient, in accordance with an embodiment of the present invention;

FIGS. 3A-B, 4A-E, and 5A-B are schematic illustrations of anchoring apparatus configured to anchor the two annuloplasty ring segments to the annulus of the patient, in accordance with an embodiment of the present invention.

DETAILED DESCRIPTION OF THE EMBODIMENTS

Reference is now made to FIGS. 1A-F, which are schematic illustrations of a system 400 for repairing a mitral valve 30, being advanced into a left atrium of a patient, in accordance with an embodiment of the present invention. Typically, a catheter 404 (FIG. 1B) is advanced into the left atrium of the patient using a percutaneous endovascular approach typically combined with continuous monitoring by electromagnetic and/or sound waves, e.g., fluoroscopy, transesophageal echo, and/or echocardiography, to maintain real-time orientation of a distal tip of the catheter within the heart of the patient. Typically, catheter 404 is transseptally advanced into the left atrium.

Catheter 404 typically comprises a 13 F catheter, although another size may be appropriate for a given patient. In some embodiments, catheter 404 is advanced through vasculature of the patient and into the right atrium using a suitable point of origin typically determined for a given patient. For example:

(1) Catheter 404 is introduced into the femoral vein of the patient, through the superior vena cava, into the right atrium of the heart, transseptally through the fossa ovalis, and finally into the left atrium;

(2) Catheter 404 is introduced into the basilic vein, through the subclavian vein to the superior vena cava, into the right atrium, transseptally through the fossa ovalis, and finally into the left atrium; or (3) Catheter 404 is introduced into the external jugular vein, through the subclavian vein to the superior vena cava, into the right atrium, transseptally through the fossa ovalis, and finally into the left atrium.

In some embodiments, catheter 404 is advanced through an inferior vena cava 22 of the patient (as shown) and into the right atrium using a suitable point of origin typically determined for a given patient.

Figure 1A:
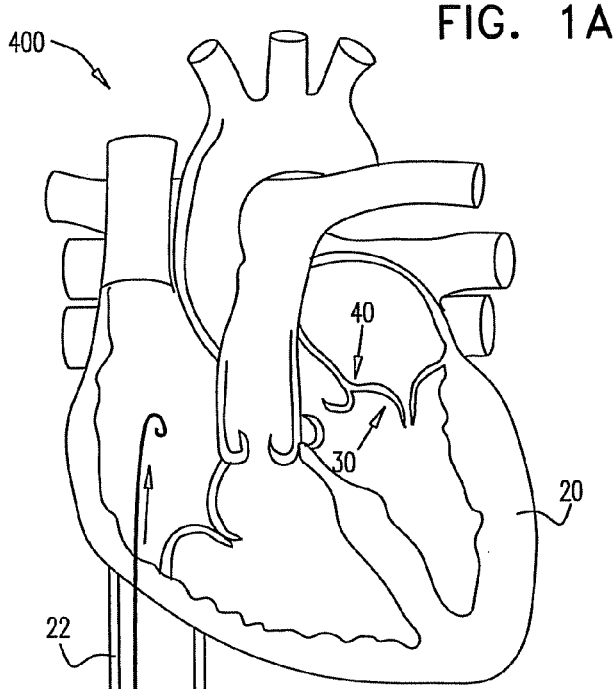
FIGS. 1A-J are schematic illustrations of transcatheter advancement and deploying of a system for repairing an annulus of the patient, in accordance with an embodiment of the present invention.
Figure 1B:
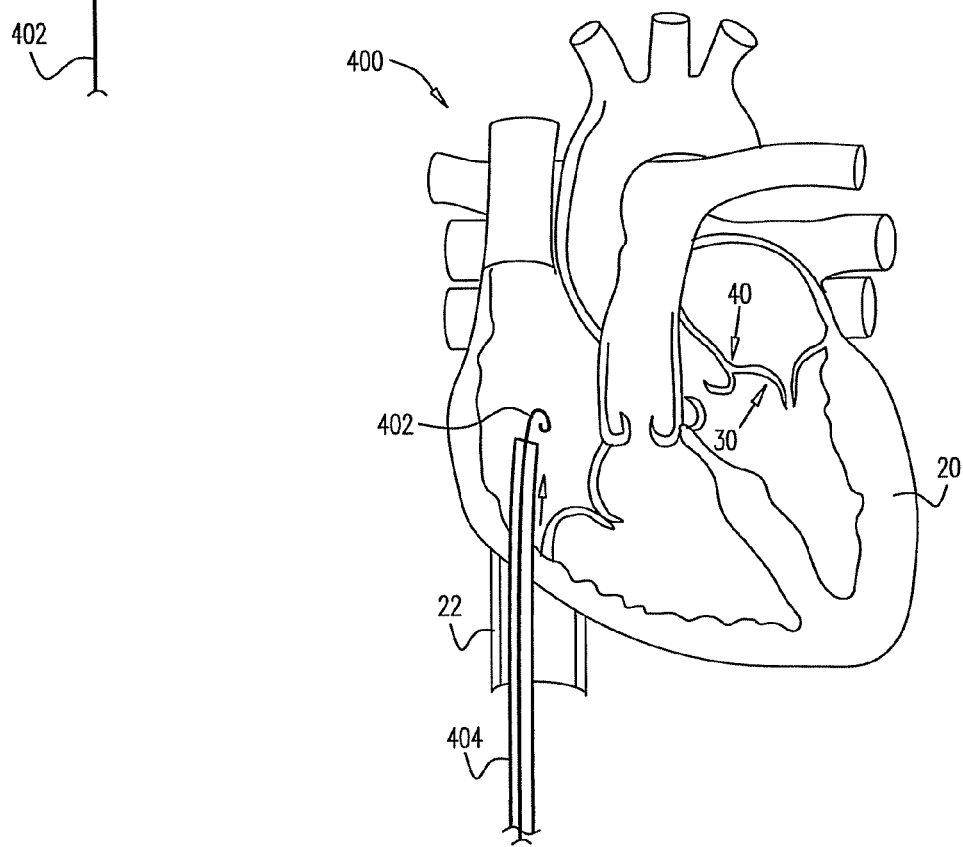
Figure 1C:
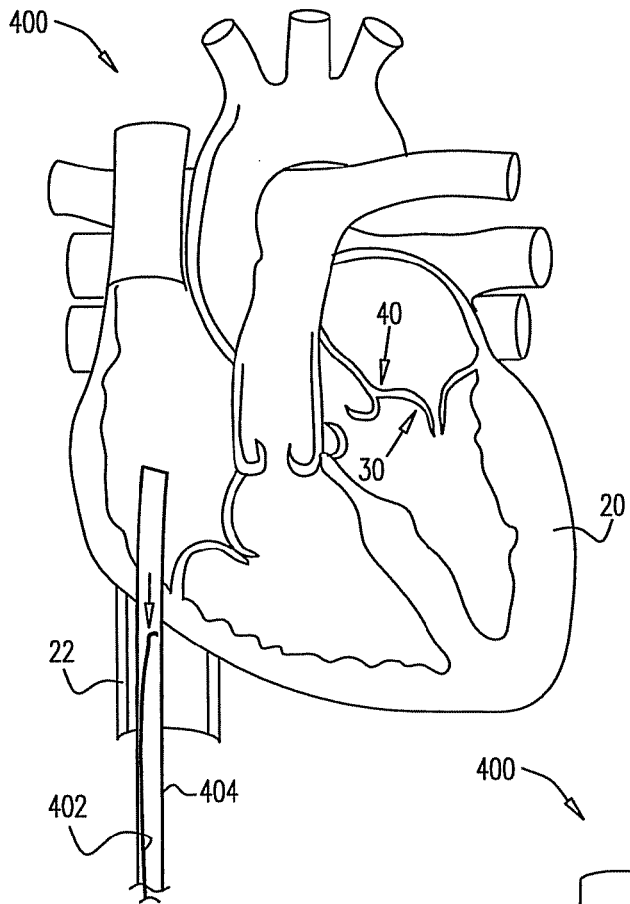
Figure 1D:
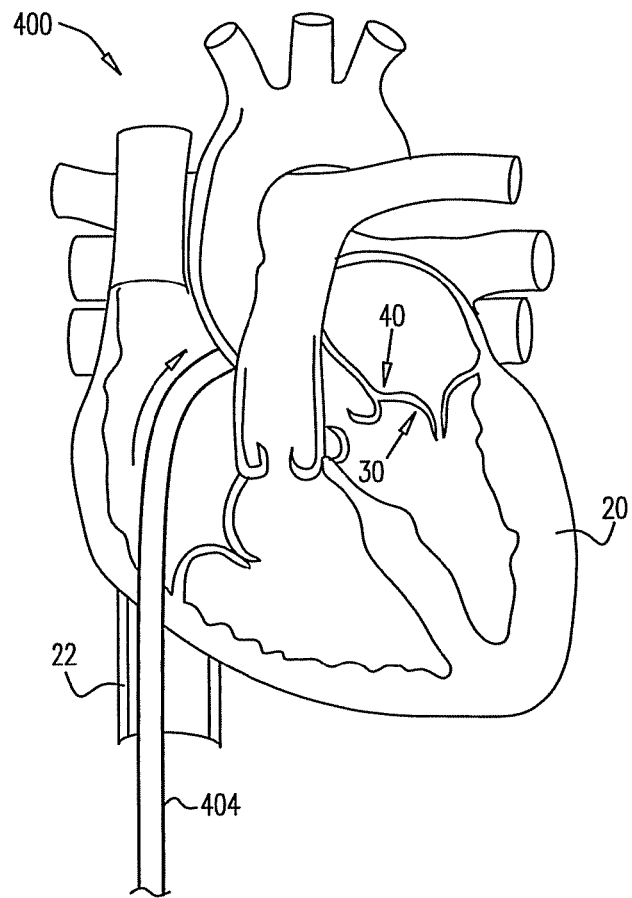

FIG. 1A shows a guide wire 402 being advanced into the right atrium of the patient. Advancement of wire 402 typically precedes advancement of catheter 404 into the right atrium of the patient. Wire 402 comprises a semi-rigid wire which provides a guide for the subsequent advancement of catheter 404 therealong and into the right atrium of the patient, as shown in FIG. 1B. Once catheter 404 has entered the right atrium, guide wire 402 is retracted and extracted from within the body of the patient (FIG. 1C). In FIG. 1D, catheter 404 is pushed distally until it reaches the interatrial septum of heart 20 of the patient.

(In this context, in the specification and in the claims, "proximal" means closer to the orifice through which catheter 404 is originally placed into the vasculature of the patient, and "distal" means further from this orifice.)

Figure 1E:
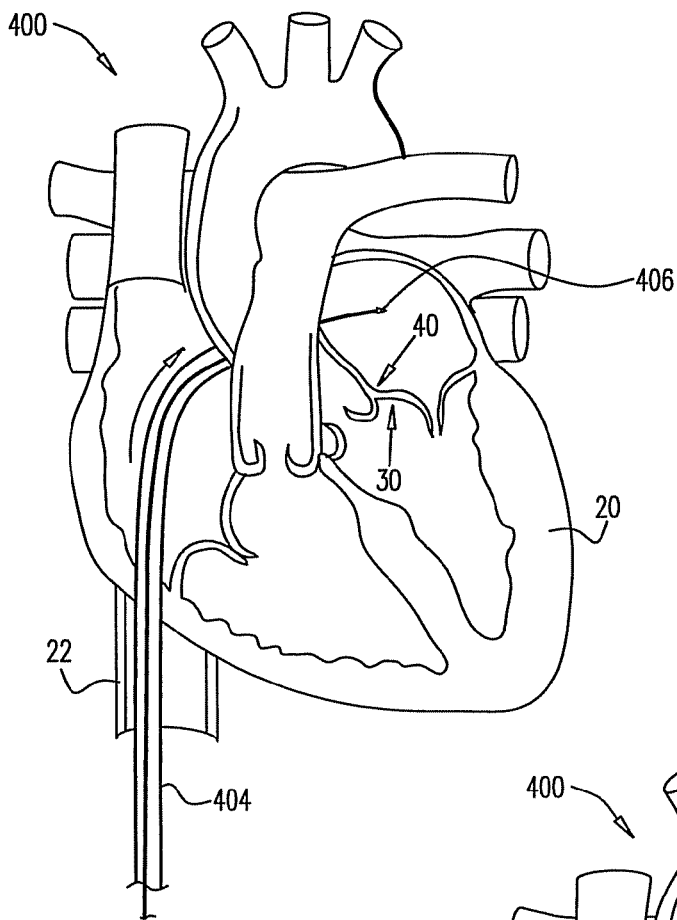
Figure 1F:
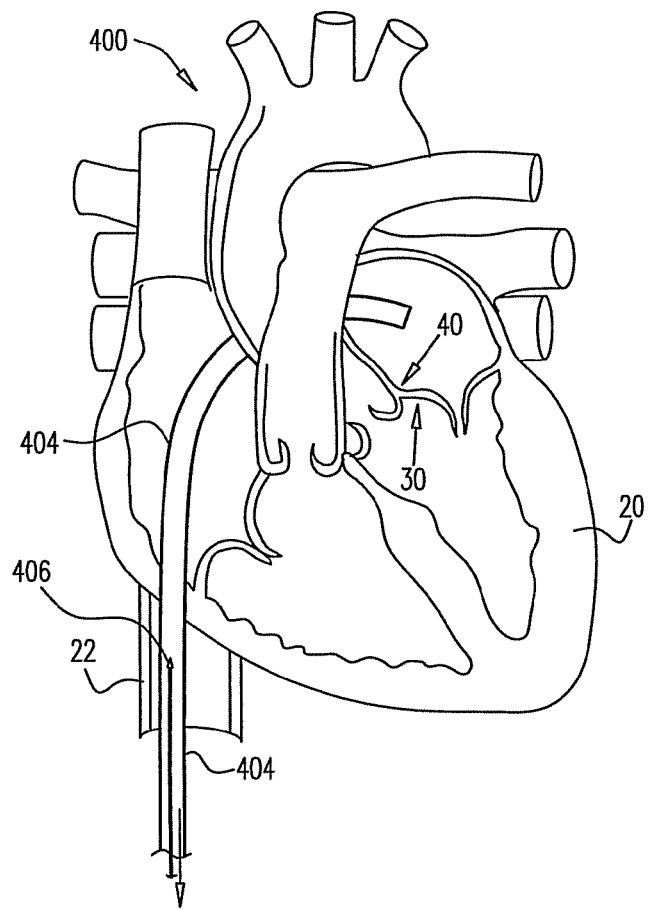

As shown in FIG. 1E, a resilient needle 406 is advanced through catheter 404 and into heart 20 of the patient. In order to advance catheter 404 transseptally into the left atrium, needle 406 first punctures the septum of heart 20 such that an opening is created which facilitates passage of catheter 404 therethrough and into the left atrium. Subsequently, a dilator (not shown) is advanced along needle 406 and toward the septum of heart 20. Typically, the dilator is shaped to define a hollow shaft for passage along needle 406, the hollow shaft being shaped to define a tapered distal end. This tapered distal end is first advanced through the hole created by needle 406. The hole is enlarged when the gradually increasing diameter of the distal end of the dilator is pushed through the hole in the septum. The advancement of catheter 404 through the septum and into the left atrium is followed by the extraction of the dilator from within catheter 404 (FIG. 1F).

Figure 1G:
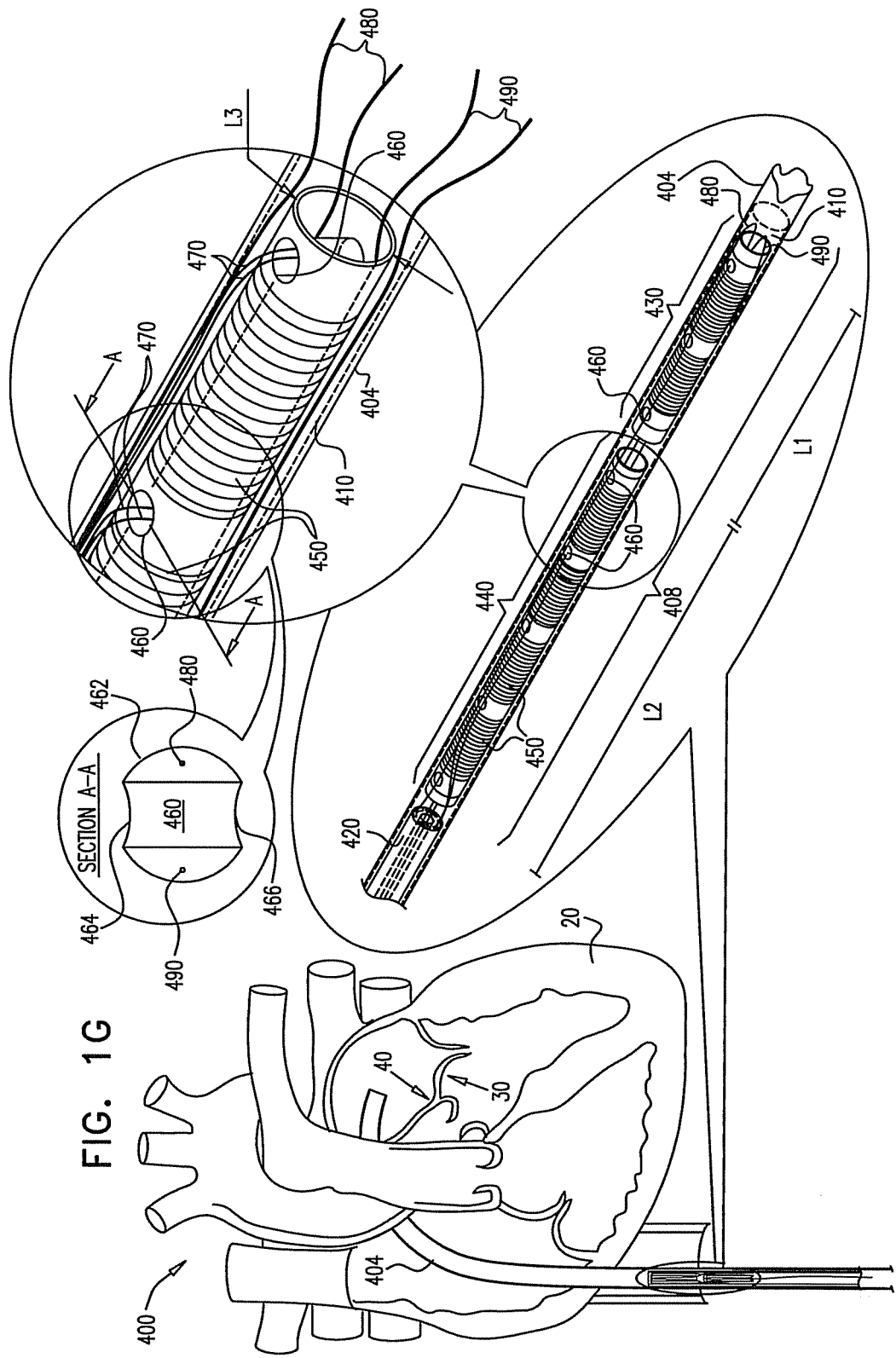

FIG. 1G is a schematic illustration of a first segment 430 and a second segment 440 of an annuloplasty structure 408 being advanced along catheter 404, in accordance with an embodiment of the present invention. Segments 430 and 440 are configured to be chronically implanted within heart 20 along an annulus 40 of mitral valve 30. Typically, segments 430 and 440 comprise a biocompatible material, e.g., nitinol, titanium, silicone, polytetrafluoroethylene (PTFE), and/or polyester graft material. Additionally, segments 430 and 440 comprise accordion-like, compressible subunits 450 which facilitate bending of the segments into a suitable configuration and compressing of the segments when they are later drawn toward one another.

In some embodiments of the present invention, segments 430 and 440 comprise coils made of stainless steel, e.g., type 304 or type 316. Suitable coil shapes include round wire coils or flat wire coils.

Prior to advancing segments 430 and 440 into the left atrium of the patient, segments 430 and 440 are loaded into an advancement catheter 410 in a substantially linear configuration, as shown in FIG. 1G. The linear configuration defines a longitudinal axis of segments 430 and 440 of structure 408. Segments 430 and 440 are typically advanced into the left atrium of the patient during a single transcatheter advancement.

During advancement of segment 430 within advancement catheter 410, segment 430 has a length L1 between about 10 mm and about 50 mm, e.g., 20 mm. Length L1 of segment 430 typically corresponds with a portion of annulus 40 at the junction between annulus 40 and the base of the anteromedial leaflet of valve 30. Similarly, second segment 440 is designated to be anchored to annulus 40 at the base of the posterolateral leaflet, and thus is sized in accordance therewith. For example, segment 440 may have a length L2 of between about 20 mm and about 80 mm, e.g., 40 mm. The respective lengths of segments 430 and 440 enable the segments to dynamically support the mitral valve in accordance with the relative motion of the anteromedial and posterolateral leaflets. Typically, segments 430 and 440 each have a diameter L3 of between about 1 mm and about 5 mm, typically between about 2.5 mm and about 3.5 mm.

Typically, segments 430 and 440 are shaped to define a lateral wall 462 that has at least one flexible hollow lumen configured for sliding advancement of at least one control wire therethrough. As shown, a first control wire 480 and a second control wire 490 are disposed within both the first and second segments 430 and 440. Typically, wires 480 and 490 function to position and adjust a relative disposition and configuration of segments 430 and 440 with respect to a configuration of annulus 40 of valve 30. Additionally, the structural and spatial configurations of each segment are controlled independently by a respective one of the first and second control wires 480 and 490. Such functions of wires 480 and 490 are described hereinbelow. As such, a diameter of control wires 480 and 490 (e.g., between about 0.2 mm and about 0.4 mm, typically, between 0.25 mm and 0.3 mm) provides the wires with the strength to control structure 408. Typically, control wires 480 and 490 comprise a resilient material capable of providing a pulling force to segments 430 and 440, e.g., nitinol or Teflon. In some embodiments, control wires 480 and 490 are Teflon-coated.

In some embodiments, first and second control tubes are disposed within both the first and second segments. Typically, the first and second control tubes are configured to function similarly to control wires 480 and 490 described herein.

Typically, lateral wall 462 of segments 430 and 440 is shaped to provide a first portion 464 and a second portion 466 generally at opposite sites of the segment when viewed in cross-section (e.g., at 12 o'clock and 6 o'clock). First and second segments 430 and 440 of annuloplasty structure 408 each comprise at least one channel 460. Channel 460 is configured to extend from first portion 464, through the given segment, to second portion 466. A respective flexible and longitudinal guide member 470 is partially disposed within each channel 460 and is used to facilitate anchoring of annuloplasty structure 408, as described hereinbelow.

Typically, guide member 470 is configured to facilitate advancement therealong of a respective anchoring structure (described hereinbelow). The anchoring structure is typically advanced along guide member 470, through channel 460, and is ultimately anchored into annulus 40 of mitral valve 30, thereby anchoring the segment to annulus 40. Typically, guide member 470 comprises a flexible metal wire, e.g., nitinol or stainless steel. In some embodiments, guide member 470 comprises a suture comprising an artificial fiber, e.g., nylon, polypropylene, Kevlar, Teflon, or polyester. Typically, each guide member 470 has a diameter of between about 0.05 mm and about 0.2 mm, e.g., 0.1 mm.

Prior to advancing segments 430 and 440 into the left atrium of the patient, advancement catheter 410 is preloaded with segments 430 and 440, with control wires 480 and 490, with guide members 470, and with a multilumen catheter 420 which is disposed proximally to segments 430 and 440. Thus, segments 430 and 440 are simultaneously conveyed toward heart 20, during a single transcatheter advancement. Typically, advancement catheter 410 comprises a 12 F catheter, although other sizes may be appropriate depending on the size of catheter 404.

Figure 1H:
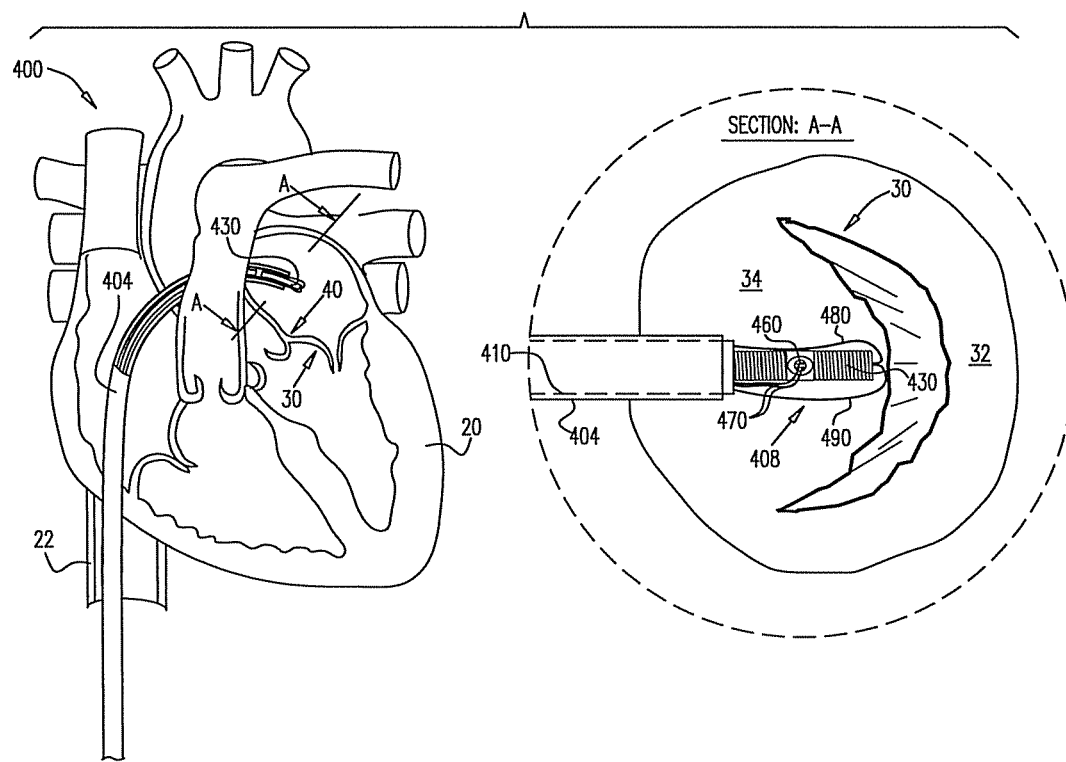
Figure 1I:
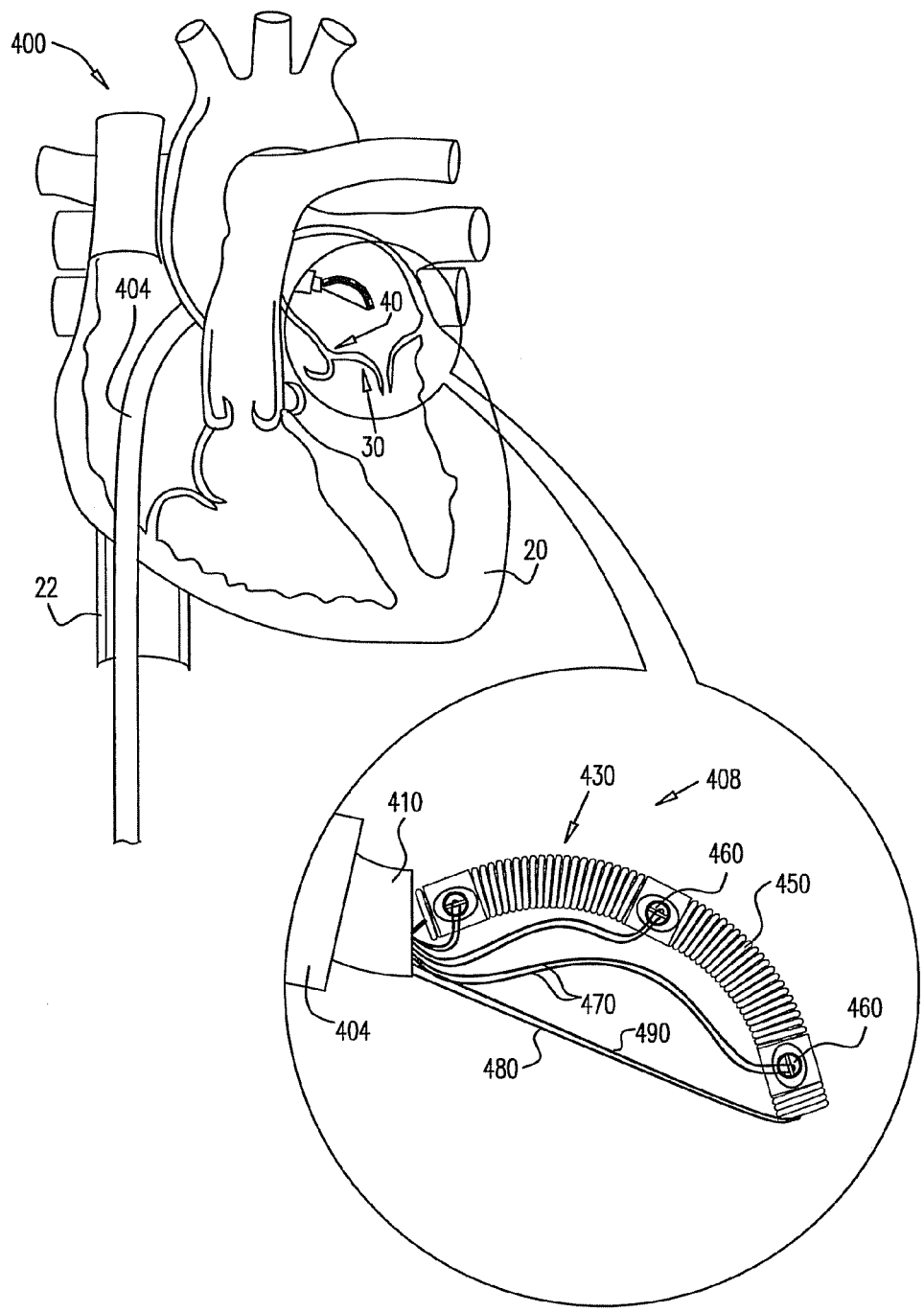

FIGS. 1H and 1I show deployment of first segment 430 of the segmented annuloplasty ring, in accordance with an embodiment of the present invention. Segments 430 and 440 are in a linear configuration within advancement catheter 410 when catheter 410 is advanced within catheter 404 and initially enters the left atrium. As shown in FIG. 1H, a distal end of catheter 410 emerges from within catheter 404. Segment 430 maintains its linear configuration as it is initially pushed from within catheter 410.

As shown by way of illustration and not limitation, each guide member 470 is looped around a bar disposed within each channel 460. The purpose of this bar is described hereinbelow.

Typically, first and second segments 430 and 440 of structure 408 are ultimately made to assume a somewhat round configuration that resembles an annuloplasty ring in structure and function.

As shown in FIG. 1I, control wires 480 and 490 are tightly pulled proximally, applying a force to segment 430 and compressing segment 430 so that it is made to assume a curved configuration. The curved configuration is thus achieved as compressible subunits 450 are compressed in response to the pulling of control wires 480 and 490. Typically, compressible subunits 450 are compressed generally in parallel with the longitudinal axis of segment 430. Such a curved configuration minimizes the possibility for segment 430 to prematurely contact walls of heart 20: (1) during deployment of system 400 within the left atrium, and (2) prior to positioning segments 430 and 440 along annulus 40.

It is to be noted that in some embodiments, segments 430 and 440 of annuloplasty structure 408 comprise a shape-memory alloy, e.g., nitinol. In these embodiments, segments 430 and 440 are introduced within catheter 410 in a straight configuration, and are each biased to assume a generally semi-circular configuration once expanded from within catheter 410. Annuloplasty structure 408 thus assumes a somewhat round configuration typically independently of the application of a proximal force to control wires 480 and 490. In such an embodiment, control wires 480 and 490 are used instead to expand the segments by separating at least a part of segment 430 from at least a part of segment 440.

Figure 1J:
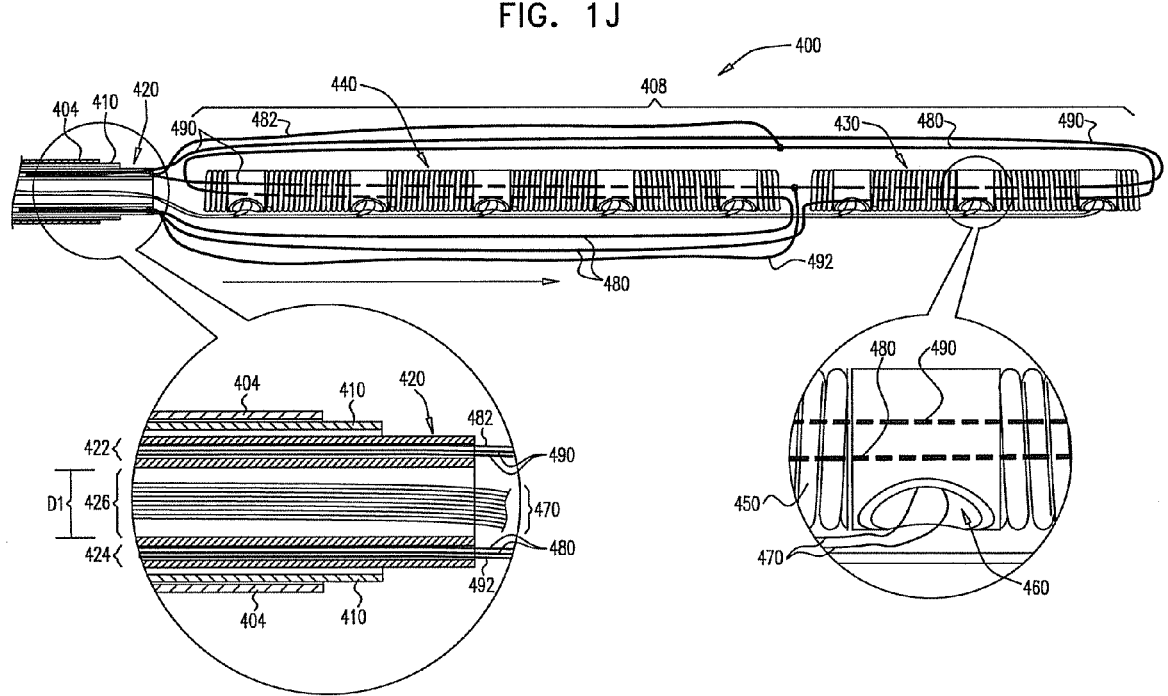

Reference is now made to FIG. 1J, which is a schematic illustration of system 400 comprising annuloplasty structure 408 and multilumen catheter 420, in accordance with an embodiment of the present invention. As shown, each control wire 480 and 490 is coupled to a respective adjustment wire 482 and 492. Adjustment wires 482 and 492 are configured to contribute to adjusting a relative disposition of segments 430 and 440 once inside the left atrium of heart 20. The functions of wires 482 and 492 are described in more detail hereinbelow.

Typically, multilumen catheter 420 is shaped to define a primary lumen 426 and secondary lumens 422 and 424. The flexible and longitudinal guide members 470 are disposed within primary lumen 426 and are exposed outside the body of the patient proximally to catheter 404. Since, in some embodiments, a respective anchoring structure is advanced along each of guide members 470, primary lumen 426 typically has a diameter D1 of between about 1.0 mm to about 3.0 mm (e.g., 1.6 mm). The diameter D1 of lumen 426 allows passage therethrough of at least one anchoring structure at a given time.

First and second portions of control wire 490 and a portion of adjustment wire 482 are disposed within secondary lumen 422 (as shown), while first and second portions of control wire 480 and a portion of adjustment wire 492 are disposed within secondary lumen 424 (as shown). Multilumen catheter 420 separates and isolates control wire 480 from control wire 490 and separates and isolates adjustment wire 482 from adjustment wire 492, thereby enabling the physician to distinguish between each of control wires 480 and 490 and between adjustment wires 482 and 492. Thus, catheter 420 helps facilitate independent control by the physician of each of the wires which ultimately determine the relative positioning of structure 408 within the left atrium of heart 20.

Reference is now made to FIGS. 2A and 2B, which are schematic illustrations of first segment 430 of structure 408 being advanced from within catheter 410, as described hereinabove with reference to FIGS. 1H and 1I, in accordance with an embodiment of the present invention.

Reference is now made to FIG. 2C, which is a schematic illustration of the deployment and expansion of segments 430 and 440, in accordance with an embodiment of the present invention. Control wires 480 and 490 are shown disposed within at least one hollow lumen of both first and second segments 430 and 440 of annuloplasty structure 480, thereby coupling the segments. In some embodiments, each of segments 430 and 440 is shaped to provide a first lumen configured for sliding advancement therethrough of wire 480, and a second lumen configured for sliding advancement of wire 490 (configuration not shown). First and second portions of control wire 480 emerge from within segments 430 and 440 at respective first ends 432 and 442 of segments 430 and 440. The first and second portions of control wire 480 are disposed within secondary lumen 424 such that first and second ends of wire 480 are exposed and controllable from outside the body of the patient. Similarly, first and second portions of control wire 490 emerge from within segments 430 and 440 at respective second ends 434 and 444 of segment 430 and 440. The first and second portions of control wire 490 are disposed within secondary lumen 422, such that first and second ends of wire 490 are exposed and controllable from outside the body of the patient.

In some embodiments, multilumen catheter 420 is shaped to provide secondary lumens 423 and 425, as shown. Typically, lumens 423 and 425 are provided for passage of supplementary instruments, e.g., for suction and/or irrigation, therethrough and into the left atrium of the patient.

Following the deployment, segments 430 and 440 are expanded by being separated in accordance with the shape of the dilated annulus. Adjustment wire 482 extends from secondary lumen 422 and is coupled at a distal end thereof to control wire 480. Typically, adjustment wire 482 is coupled to a portion of wire 480 that is disposed at a junction between respective second ends 434 and 444 of segments 430 and 440. Similarly, adjustment wire 492 extends from secondary lumen 424 and is coupled at a distal end thereof to control wire 490. Typically, adjustment wire 492 is coupled to a portion of control wire 490 that is disposed at a junction between respective first ends 432 and 442 of segments 430 and 440. Typically, adjustment wires 482 and 492 are irreversibly coupled, e.g. knotted or otherwise fixed, to control wires 480 and 490, respectively. In some embodiments, adjustment wires 482 and 492 are looped around control wires 480 and 490, respectively.

The separating of segments 430 and 440 occurs when the physician pushes control wires 480 and 490 while pushing adjustment wires 482 and 492. Thus, adjustment wires 482 and 492 provide an auxiliary pushing force which helps expand segments 430 and 440. Such pushing of the control wires feeds greater portions of control wires 480 and 490 into segments 430 and 440. The relaxed configuration of control wires 480 and 490 is shown in FIG. 2C, while the taut configuration thereof is shown in FIG. 2B. Typically, segments 430 and 440 expand annularly as increasing lengths of control wires 480 and 490 are pushed and fed into segments 430 and 440.

In some embodiments of the present invention, adjustment wires 482 and 492 are pulled to elevate portions of segments 430 and 440, such that the segments conform to the shape of annulus 40. For example, pulling adjustment wire 482 elevates the portion of control wire 480 which is disposed between segments 430 and 440. In response to the pulling, second ends 434 and 444 of segments 430 and 440, respectively, are elevated.

Control wires 480 and 490 enable the physician to control a relative disposition of second ends 434 and 444 and first ends 432 and 442 of segments 430 and 440, respectively. For example, distal pushing of the first and second ends of control wire 480 distances second ends 434 and 444 of segments 430 and 440, respectively. Similarly, distal pushing of the first and second ends of control wire 490 distances first ends 432 and 442 of segments 430 and 440, respectively. It is to be noted that the use of two discrete control wires allows for independent control of the distance that separates first ends 432 and 442 and the distance that separates second ends 434 and 444 of segments 430 and 440.

Additionally, pulling on respective ends of control wires 480 and 490 shapes segments 430 and 440 in accordance with the curved structural conformation of annulus 40 at a given site destined for anchoring of a respective one of the segments thereto. For example, pulling on a first end of control wire 490 and on a first end of control wire 480 curves segment 430 by drawing together first end 432 and second end 434, respectively, of segment 430. Thus, segment 430 is compressed at least in part, and is made to assume a shape according to the curvature of the annulus at the base of the anteromedial leaflet.

Figure 2D:
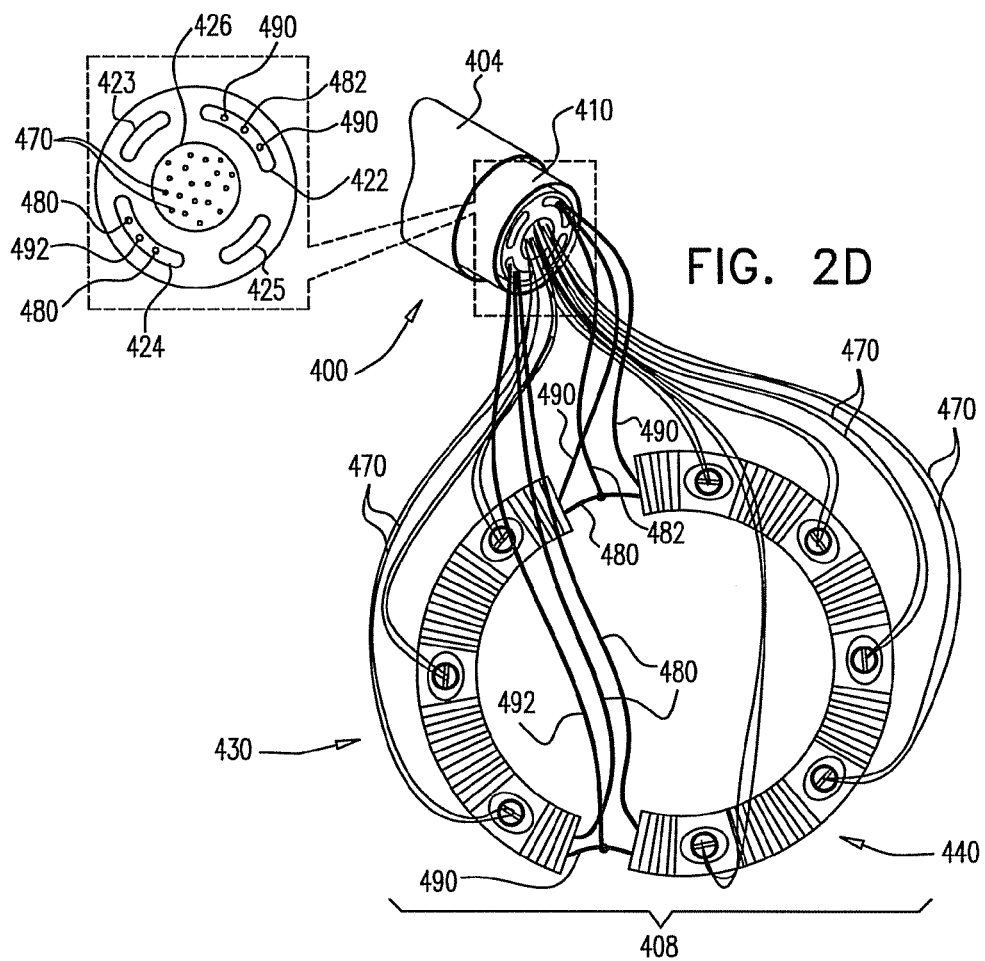

Reference is now made to FIG. 2D, which is a schematic illustration of the deployment and expansion of segments 430 and 440 as described hereinabove with reference to FIG. 2C, with the exception that structure 408 is optionally rotated as appropriate about an axis of annulus 40, in accordance with an embodiment of the present invention. Guided by echocardiography, the physician assesses the relative disposition of segments 430 and 440 with respect to annulus 40 of heart 20. Multilumen catheter 420 is configured to be rotatable 360 degrees about a longitudinal axis thereof. By rotating multilumen catheter 420, the segments are positioned properly with respect to the annulus. That is, segment 440 is positioned above a portion of annulus 40 at the base of the posterolateral leaflet, while segment 430 is positioned above a portion of annulus 40 at the base of the anteromedial leaflet.

Figure 2E:
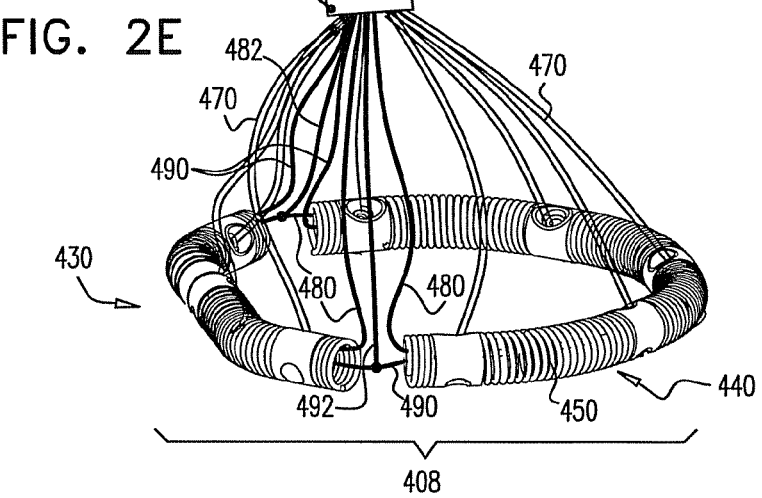

FIG. 2E shows catheter 410 comprising a steering wire 500, in accordance with an embodiment of the present invention. Typically, a distal end of steering wire 500 is coupled to a distal end of catheter 410. A proximal end of wire 500 is disposed at a site outside the body of the patient, enabling the physician to steer the distal end of catheter 410. Following the deployment and expansion of annuloplasty structure 408, multilumen catheter 420 is retracted slightly within advancement catheter 410. Retracting multilumen catheter 420 frees the lumen of the distal end of catheter 410, thereby restoring flexibility to the distal end of catheter 410 and enabling proper steering thereof. Structure 408 is pushed toward annulus 40 by pushing on both catheter 410 and on wires 480 and 490. Additionally, the structure is properly aligned with annulus 40 by steering and/or rotating the distal tip of catheter 410.

Figure 2F:
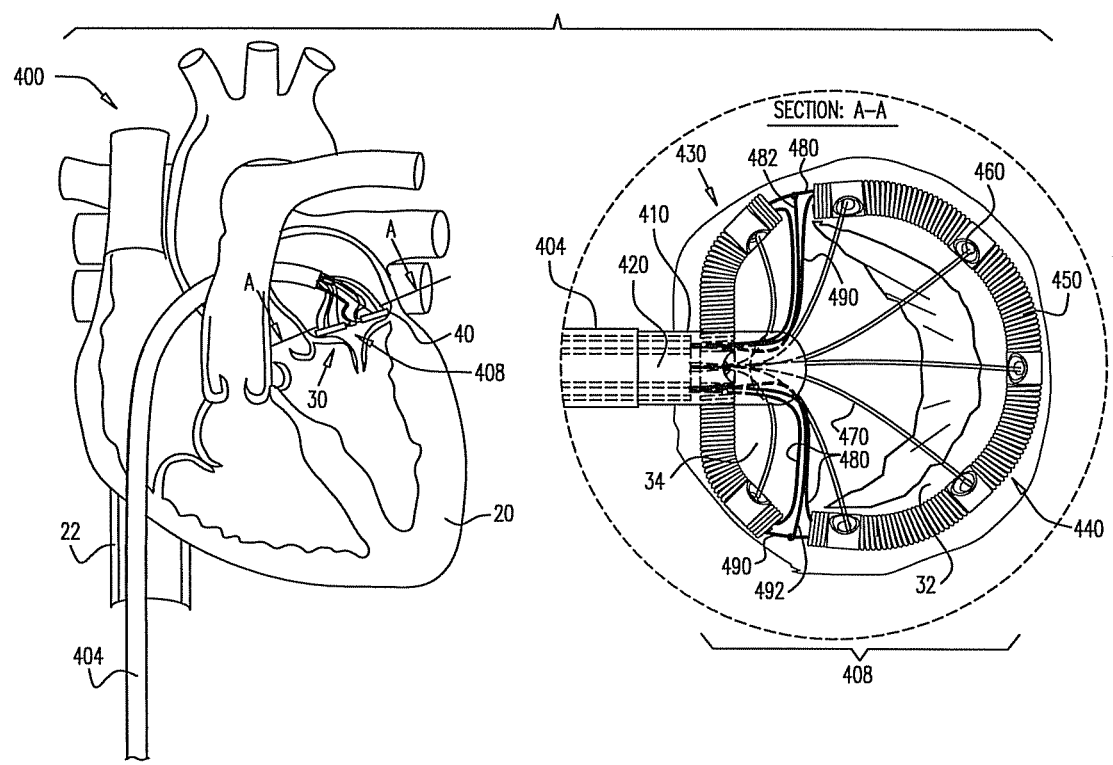

FIG. 2F shows system 400 following the aligning of segments 430 and 440 with annulus 40, in accordance with an embodiment of the present invention. Segment 440 is aligned against the base of posterolateral leaflet 32 at the annulus, and segment 430 is aligned against the base of anteromedial leaflet 34 at the annulus. Segments 430 and 440 are shown prior to anchoring thereof to annulus 40. Multilumen catheter 420 is shown in a slightly retracted state within catheter 410.

Figure 3A:
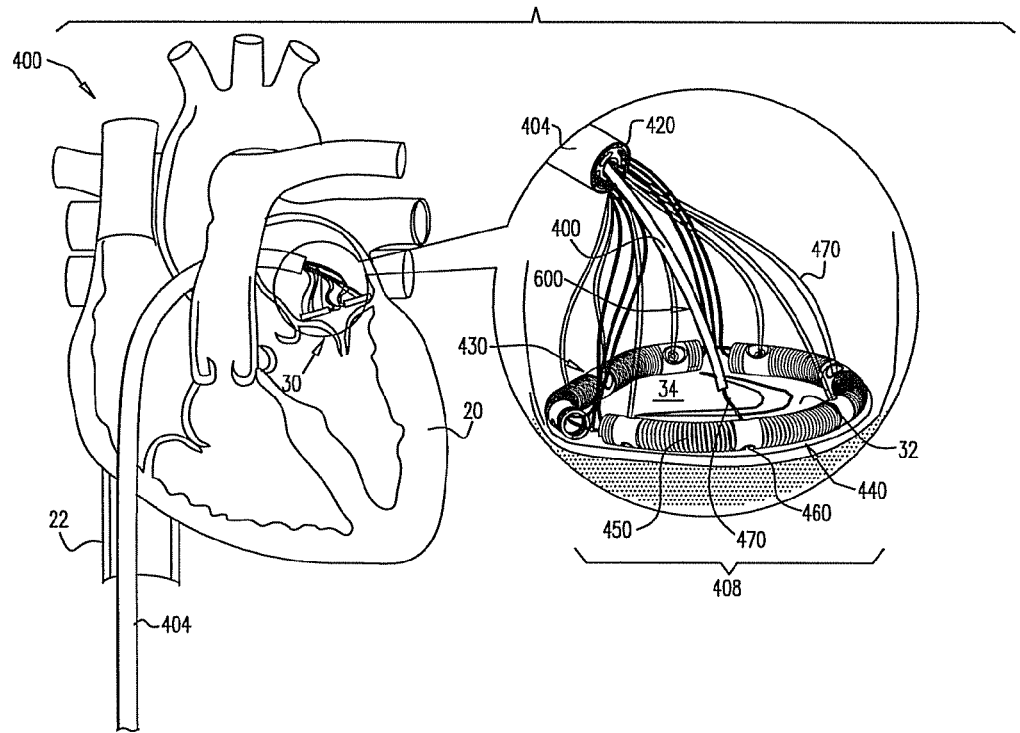
Figure 3B:
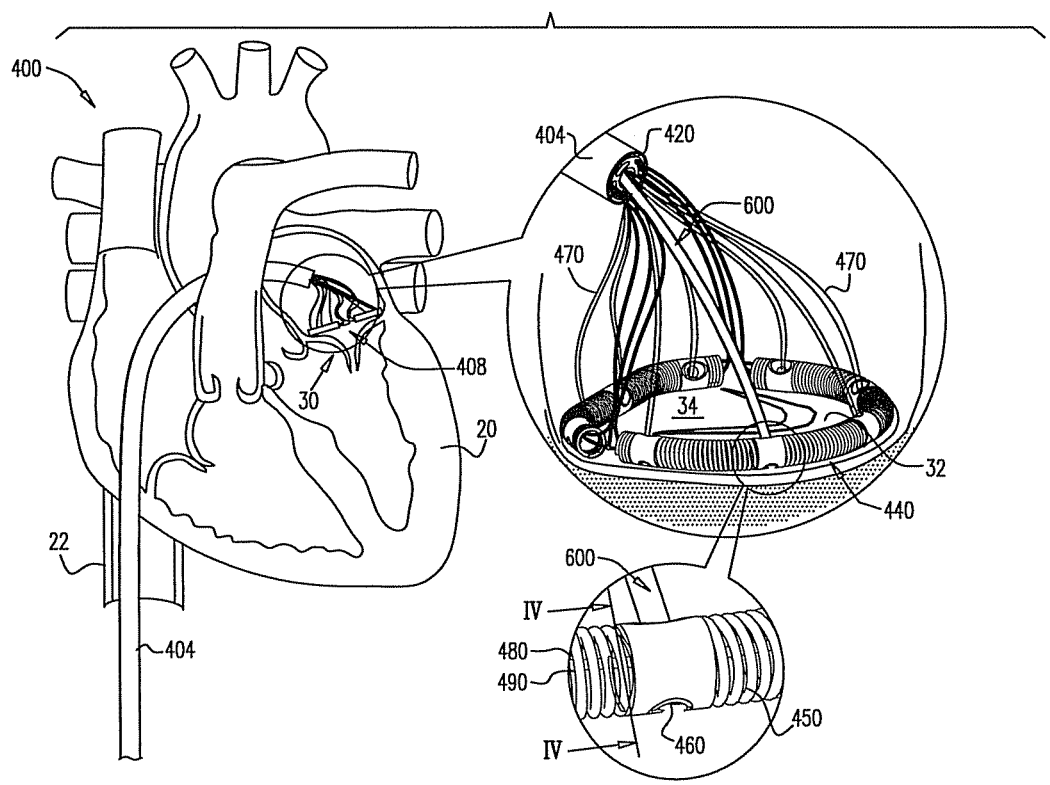

Reference is now made to FIGS. 3A and 3B, which are schematic illustrations of system 400 comprising an anchoring system 600, in accordance with an embodiment of the present invention. Once advancement catheter 410 has positioned segments 430 and 440 in their proper orientation with respect to annulus 40, catheter 410 is retracted slightly within catheter 404 and a distal end of multilumen catheter 420 is exposed. At a site proximal to catheter 404, and outside the body of the patient, the physician slides a first anchoring system 600 around both ends of a first flexible and longitudinal guide member 470. Anchoring system 600 is advanced through primary lumen 426 of multilumen catheter 420. Anchoring system 600 is advanced along guide member 470 and subsequently inserted, in part, into channel 460, as shown in FIG. 3B.

Reference is now made to FIGS. 4A-E, which are schematic illustrations of anchoring system 600, in accordance with an embodiment of the present invention. FIG. 4A shows a bar 710 disposed within channel 460. Typically, bar 710 is disposed perpendicularly to an axis of channel 460, and at the base of the channel. It is to be noted that bar 710 is disposed parallel to the longitudinal axis of segment 440 (or segment 430) by way of illustration and not limitation. For example, bar 710 may be disposed perpendicularly to the axis of segment 440. Guide member 470 is disposed within channel 460 and is reversibly coupled to structure 408 via bar 710. Typically, guide member 470 is looped around bar 710 prior to the advancement of structure 408 into the body of the patient. When structure 408 is disposed within heart 20, both ends of guide member 470 are exposed outside the body of the patient, thus enabling the physician to slide anchoring system 600 around both ends of member 470 and therealong toward annulus 40 of heart 20.

FIG. 4B shows anchoring system 600 comprising an outer tube 610 housing an advancement tube 620, which is reversibly coupled to an anchoring structure 740. Typically, anchoring structure 740 comprises a helical element whose proximal end is tightly wrapped around a distal end of advancement tube 620. Outer tube 610 typically prevents radial expansion of anchoring structure 740 within primary lumen 426 of multilumen catheter 420 as element 740 is advanced therein. Anchoring system 600 is advanced within channel 460, as shown in FIG. 4C.

Reference is now made to FIG. 4D. Anchoring of anchoring structure 740 begins when the physician rotates advancement tube 620 about a longitudinal axis thereof. Such rotation corkscrews a distal portion of the helical element around and beyond bar 710 and subsequently into annulus 40 of the patient.

Reference is made to FIGS. 4A and 4B. Typically, channel 460 has a diameter D2, e.g., between about 0.8 mm and 1.2 mm, typically 1.0 mm. Diameter D2 is thus sized in order to enable passage of anchoring structure 740 through channel 460. Typically, anchoring structure 740 has a diameter D3 of between about 0.5 mm and 1.5 mm, e.g., 1 mm. Typically, each coil of the coiled, helical element has a diameter D4 of between about 0.05 mm and 0.5 mm, e.g., 0.2 mm.

Reference is again made to FIG. 4B. Typically, the helical element is shaped to define at least two adjacent distal rotational subunits 720 and at least two adjacent proximal rotational subunits 730. A distance Di1 (e.g., between about 0.3 mm and about 0.6 mm) between adjacent distal rotational subunits 720 is typically greater than a distance Di2 (e.g., between about 0 mm and about 0.4 mm) between adjacent proximal rotational subunits 730. Typically a diameter of bar 710 is less than distance Di1 and greater than distance Di2. Distance Di1 enables distal rotational subunits 720 to be corkscrewed around bar 710 and subsequently into annulus 40 of the patient. Distance Di2 is typically less than a diameter of bar 710, and therefore restricts proximal rotational subunits 730 from being corkscrewed fully around bar 710 and into annulus 40.

During an attempt to corkscrew proximal rotational subunits 730 around bar 710, bar 710 restricts the rotation of subunits 730 therearound and applies a counterforce to a torque applied by rotation of tube 620. The counterforce applied by bar 710 expands proximal subunits 730 radially such that subunits 730 are no longer wrapped tightly around the distal end of tube 620. Following the expansion of subunits 730, anchoring structure 740 is released from tube 620, typically by pulling on tube 620 while continuing to apply a rotational, helix-expanding force to proximal subunits 730. Tube 620 is then pulled proximally along guide member 470 and extracted from within the body of the patient, as shown in FIG. 4E. During the removal of tube 620 from heart 20, guide member 470 typically remains within system 400, although it is optionally removed at the same time as tube 620.

In some embodiments of the present invention, a few rotational subunits of the helical element are wrapped around a distal end of tube 620, while the remaining rotational subunits extend distally from the distal end of tube 620. Typically, a smaller number of rotational subunits are wrapped around tube 620 than the number of rotational subunits that extend distally from the distal end of tube 620 and are not wrapped around the distal end of tube 620. As shown by way of illustration and not limitation, three rotational subunits are wrapped around the distal end of tube 620, while four rotational subunits are disposed distally to the distal end of tube 620. The rotational subunits wrapped around the distal end of tube 620 generally provide enough frictional force to maintain their position around the distal end of tube 620.

A protrusion (not shown) is typically disposed along the distal end of tube 620 adjacent to the proximal-most tip of the helical element of anchoring structure 740. During initial implantation of the anchoring structure within annulus 40 of the patient (i.e., as tube 620 is rotated), the protrusion applies a circumferentially-directed pushing force to the proximal-most tip of the helical element. By pushing on the proximal-most tip of the helical element, the protrusion typically adds to the frictional force described above, in order to rotate anchoring structure 740. One or both of these forces enable a distal end of structure 740 to puncture annulus 40. As anchoring structure 740 is advanced into tissue of annulus 40, the proximal end of anchoring structure 740 slides distally along the distal end of tube 620 and away from the protrusion.

Following implantation within annulus 40 of distal rotational subunits 720, the distal end of tube 620 is impeded by bar 710. The physician continues to rotate tube 620 such that the proximal-most tip of anchoring structure 740 continues to slide distally from the protrusion while the entire anchoring structure 740 continues to be advanced distally within tissue of annulus 40. During the continued rotation of tube 620, fewer rotational subunits are wrapped around the distal end of tube 620, thereby reducing friction between anchoring structure 740 and the distal end of tube 620. After a sufficient number of rotations, the minimal friction between structure 740 and the distal end of tube 620 enables the physician to pull on tube 620 in order to detach tube 620 from anchoring structure 740.

It is to be understood that use of a helical anchoring structure 740 is described herein by way of illustration and not limitation, and that the scope of the present invention includes the use of other apparatus for anchoring annuloplasty structure 408 to annulus 40. For example, anchoring structure 740 may comprise a screw, harpoon, barb, or any other anchoring structure known in the art. In some embodiments, anchoring structure 740 comprises a wire configured to penetrate annulus 40 in a generally straight configuration and to subsequently assume a curved configuration once inside tissue of annulus 40.

Figure 5A:
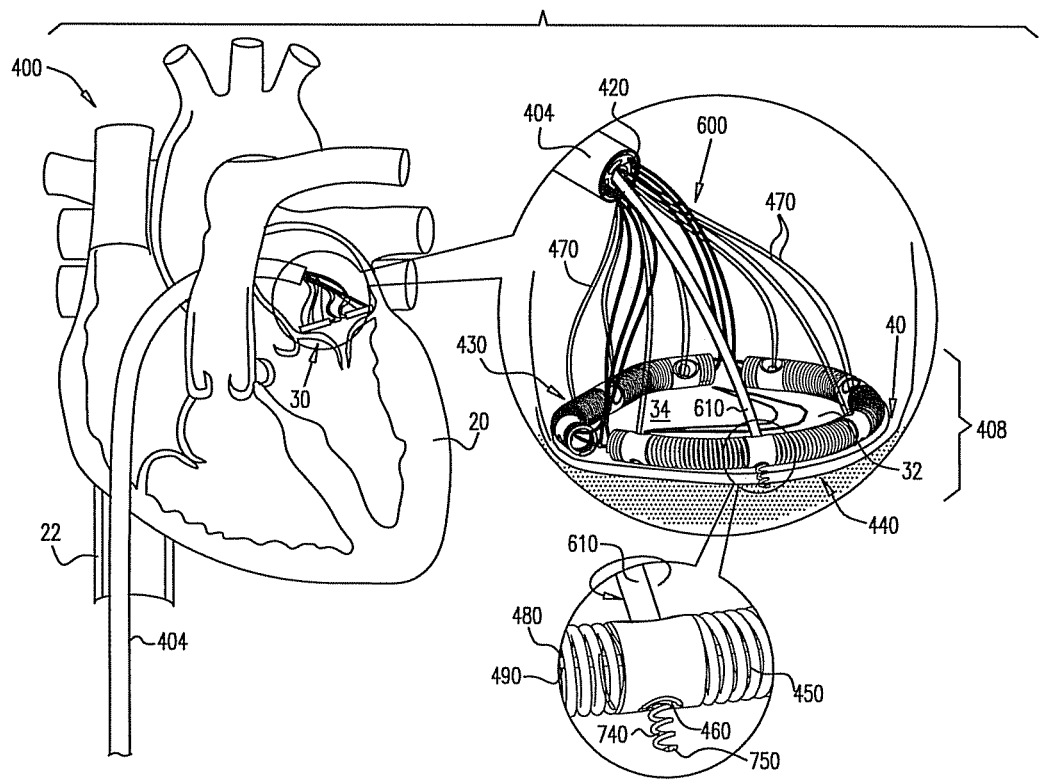
Figure 5B:
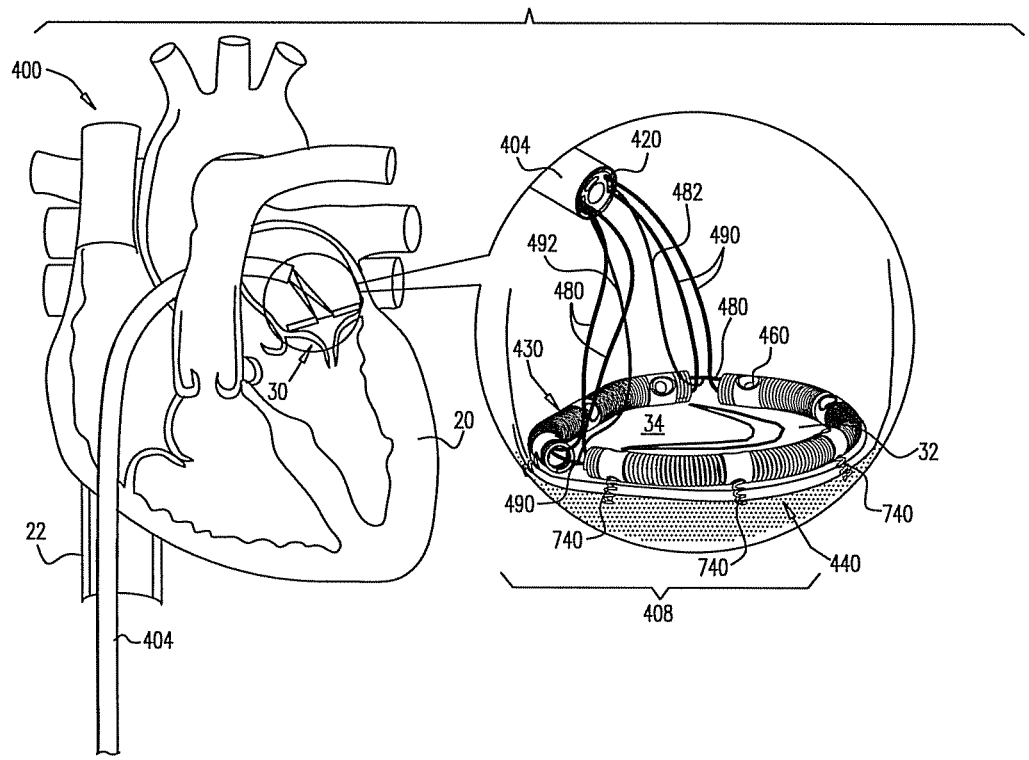

Reference is now made to FIGS. 5A-B, which are schematic illustrations of anchoring system 600, which anchors segments 430 and 440 to annulus 40 of heart 20, in accordance with an embodiment of the present invention. FIG. 5A shows segment 440 being anchored, via anchoring system 600, to annulus 40 at the base of posterolateral leaflet 32. A respective anchoring system 600 is sequentially advanced along each guide member 470 until both segments 430 and 440 are anchored to annulus 40, and tubes 620 and guide members 470 are withdrawn.

As shown, the helical element of anchoring structure 740 comprises a pointed distal tip 750 configured to puncture tissue of annulus 40 in order to enable screwing of structure 740 within annulus 40 of the patient. In some embodiments, distal tip 750 comprises a barb or anchoring structure 740 comprises a plurality of barbs, configured to provide a lock between structure 740 and annulus 40.

Following the anchoring of each structure 740 within annulus 40, each guide member 470 is decoupled from the respective bar 710. For embodiments in which guide member 470 is looped around bar 710, guide member 470 is decoupled from bar 710 when the physician pulls on a first end of guide member 470 from a site outside the body of the patient. Guide member 470 slides around bar 710 until it is extracted from within the body of the patient.

In some embodiments, a first end of guide member 470 comprises a material configured to dissolve when exposed within heart 20 of the patient. In such an embodiment, guide member 470 is typically not looped around bar 710, rather, it is coupled at its first end to bar 710 while a second end thereof is disposed outside the body of the patient. Following anchoring of structure 740 to annulus 40 as described hereinabove, the first end of guide member 470 dissolves, thereby decoupling guide member 470 from bar 710. Guide member 470 is then pulled from its second end until the first end is extracted from within the body of the patient.

In some embodiments, a first end of guide member 470 is coupled to one of the segments, prior to placement in the patient's body, by, for example, passing through channel 460 and being attached to an external surface of the segment. Alternatively, guide member 470 comprises a "T"-shaped anchor at a distal end of guide member 470, which passes through channel 460 and inhibits proximal motion of the "T"-shaped anchor through the channel. In such an embodiment, guide member 470 is typically not looped around bar 710. Typically, a second end of guide member 470 is disposed outside the body of the patient. Following anchoring of structure 740 to annulus 40 as described hereinabove, the physician pulls on the second end of guide member 470 in order to tear the guide member at a pre-weakened point on the guide member, typically slightly proximal to the segment. Guide member 470 is then extracted from within the body of the patient while the distal-most portion of guide member 470 that is attached to the external surface of the segment, or the "T"-shaped anchor, remains disposed within structure 408.

Figure 5C:
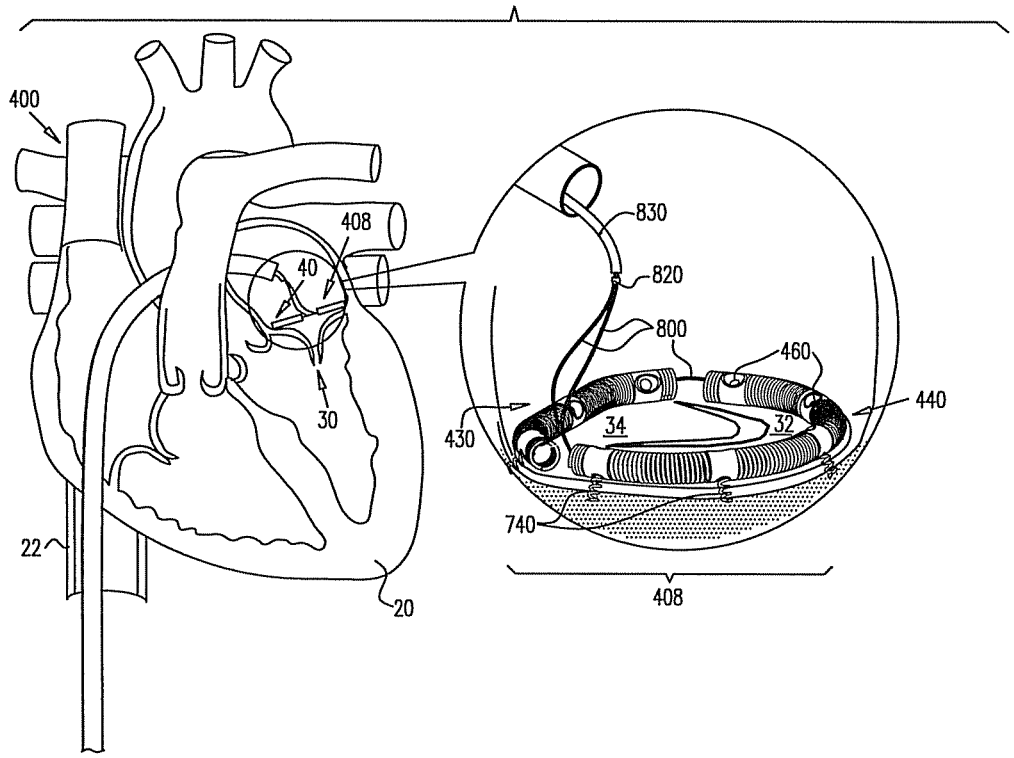
FIGS. 5C-D are schematic illustrations of the drawing together and locking of the two segments of the annuloplasty ring to the annulus of the patient, in accordance with an embodiment of the present invention.

Reference is now made to FIG. 5C, which is a schematic illustration of system 400, comprising a tensile suture 800 configured for sliding advancement through segments 430 and 440, in accordance with an embodiment of the present invention. One of control wires 480 or 490, e.g., control wire 480, is extracted from within segments 430 and 440 when the physician pulls on a first end of wire 480. Subsequently, the physician replaces control wire 490 with tensile suture 800 by (a) tying a first end of suture 800 to a first end of wire 490, and then (b) pulling on a second end of wire 490. The physician pulls wire 490 until the first end of suture 800 has replaced control wire 490 in segments 430 and 440, e.g., until suture 800 is once again exposed outside the body of the patient. As shown in FIG. 5C, a portion of suture 800 remains disposed within both segments 430 and 440. Tensile suture 800 comprises a flexible material, e.g., nitinol, Kevlar, titanium, or polytetrafluoroethylene (PTFE), and is configured to reside chronically within segments 430 and 440. For example, suture 800 may comprise a braided polyester suture (e.g., Ticron). Additionally, suture 800 is configured to withstand cardiac pressures and constant motion of segments 430 and 440 that result from the motion of annulus 40. As such, suture 800 typically has a relatively thick diameter of between about 0.1 mm and about 1.0 mm, typically between about 0.3 mm and about 0.6 mm.

In some embodiments, two tensile sutures 800 reside chronically within segments 430 and 440. In such an embodiment, a first tensile suture replaces control wire 480, and a second tensile suture replaces control wire 490. Control wires 480 and 490 are replaced as described hereinabove.

In any embodiment, using tactile feedback and optionally in combination with fluoroscopic imaging, first and second ends of suture(s) 800 are pulled to an extent that is based on (a) the level of dilation of the preoperative mitral valve, and/or (b) real-time monitoring of regurgitation minimization.

FIG. 5C shows a lock 820 being advanced around first and second portions of suture 800, in accordance with an embodiment of the present invention. Lock 820 secures together segments 430 and 440 of annuloplasty structure 408, thereby defining its final configuration within annulus 40 of mitral valve 30. The excess portions of tensile suture 800 are clipped proximally to lock 820 and are extracted from the body via catheter 404. Following clipping, first and second ends of suture 800 remain accessible for future tightening together of segments 430 and 440 upon need therefor. In some embodiments, the first and second ends of suture 800 are located using fluoroscopy or any other method described herein.

Figure 5D:
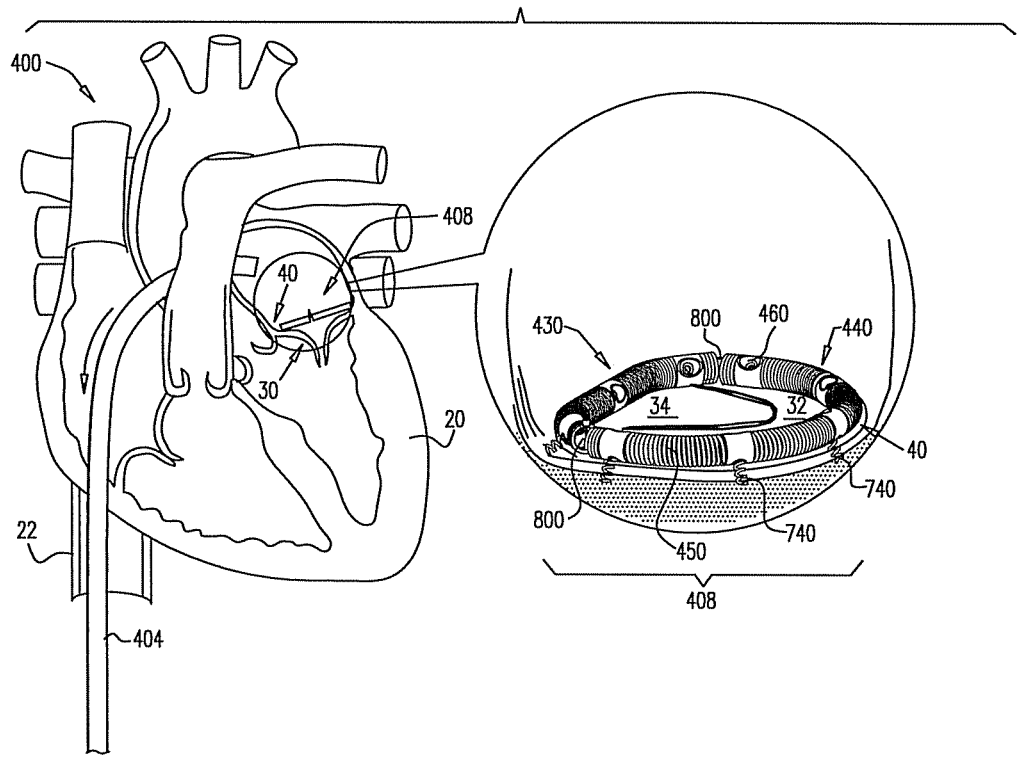

FIG. 5D shows annuloplasty structure 408 in a closed state, in accordance with an embodiment of the present invention. By reducing a circumference of annulus 40, leaflets 32 and 34 are lifted and/or drawn toward one another to prevent recurring dilation of mitral valve 30, restore leaflet coaptation, and reduce mitral regurgitation.

It is to be noted that in an embodiment of the present invention, guide members 470 comprise a screw at a distal end thereof. Guide member 470 in this embodiment is suitable for conveying torque, such that by rotating the proximal end of the guide member from outside the body of the patient, the screw at the distal end is screwed into the annulus. Following anchoring of the screw to the annulus of the patient, the guide member is clipped proximally to the screw and is extracted from within the body of the patient. In such an embodiment, guide member 470 is configured to anchor structure 408 to annulus 40 independently of bar 710 described hereinabove.

It is to be noted that the scope of the present invention is not limited to minimally-invasive procedures (e.g., transcatheter procedures such as percutaneous or intercostal penetration procedures), and includes applications in which system 400 is applied in invasive procedures such as open heart surgery.

It is to be further noted that system 400 may be used to treat valves other than mitral valve 30. For example, system 400 may be used to treat an aortic valve of the patient.

The scope of the present invention includes embodiments described in one or more of the following:

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

a US provisional patent application to Gross et al., entitled, "Segmented ring placement," filed Oct. 29, 2007; and a PCT patent application to Gross et al., entitled, "Segmented ring placement," filed on even date herewith.

All of these applications are incorporated herein by reference. Techniques described herein can be practiced in combination with techniques described in one or more of these applications.

For some applications, techniques described herein are practiced in combination with techniques described in one or more of the references cited in the Background section and Cross-References section of the present patent application. All references cited herein, including patents, patent applications, and articles, are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for repairing a valve of a body of a patient, the valve including an annulus and at least first and second leaflets, comprising:
    at least a first segment and a second segment of an annuloplasty structure, the first segment being shaped to define at least one first lumen, and the second segment being shaped to define at least one second lumen that is separate from the at least one first lumen of the first segment; and
    at least a first and a second control wire, wherein:
        a first slidable coupling arrangement, coupling the first control wire and the first segment via the at least one first lumen, and a second slidable coupling arrangement, coupling the second control wire and the second segment via the at least one second lumen, facilitate control by the control wires of relative dispositions of the first and second segments, at least in part in response to an application of pulling forces to the control wires.

2. The apparatus according to claim 1, wherein:
    the first segment defines a first lateral wall that surrounds the first lumen,
    the second segment defines a second lateral wall that surrounds the second lumen,
    for each of the first and second lateral walls of each segment, the lateral wall has a first and a second portion, and the segment is shaped to provide a channel extending from the first portion to the second portion, and
    the apparatus further comprises a bar configured to be disposed within the channel.

3. The apparatus according to claim 2, further comprising a flexible longitudinal guide member configured to be removably coupled to the bar.

4. The apparatus according to claim 3, further comprising an anchoring structure, wherein, while the guide member is disposed within the body of the patient, the anchoring structure is configured to be advanced via the guide member, through the channel, and subsequently anchored to the annulus of the patient.

5. The apparatus according to claim 4, wherein, while the guide member is disposed within the body of the patient, the anchoring structure is configured to be advanced along the guide member from a site outside the body of the patient.

6. The apparatus according to claim 5, wherein, while the guide member is disposed within the body of the patient, the guide member is configured to be decoupled from the bar subsequent to the anchoring of the anchoring structure to the annulus.

7. The apparatus according to claim 1, further comprising at least first and second flexible longitudinal guide members, the first and second guide members configured to be removably coupled to the first and second segments, respectively, each guide member being configured to facilitate anchoring of the respective segment to the annulus of the patient.

8. The apparatus according to claim 1, wherein the first and second control wires are configured to expand the first and second segments.

9. The apparatus according to claim 1, wherein the first and second control wires are configured to facilitate positioning of the first and second segments along the annulus.

10. The apparatus according to claim 1, wherein the first and second segments are configured to be advanced toward the valve of the patient in a generally straight configuration of the first and second segments, and wherein the first and second control wires are configured to pull the first and second segments into a curved configuration.

11. The apparatus according to claim 1, wherein the first control wire is configured to compress the first segment at least in part in response to an application of a pulling force to at least a portion of the first control wire, and wherein the second control wire is configured to compress the second segment at least in part in response to an application of a pulling force to at least a portion of the second control wire.

12. The apparatus according to claim 4, wherein:
    the anchoring structure comprises a helical element, the helical element shaped to define at least two adjacent distal rotational subunits and at least two adjacent proximal rotational subunits, wherein a distance between the two adjacent distal rotational subunits is greater than a distance between the two adjacent proximal rotational subunits,
    the distance between the distal rotational subunits enables the distal rotational subunits to be corkscrewed around the bar and subsequently into tissue of the patient, and
    the distance between the proximal rotational subunits restricts the proximal rotational subunits from being corkscrewed into tissue of the patient.

13. The apparatus according to claim 1, further comprising a catheter, wherein the first and second segments are configured to be conveyed simultaneously through the catheter and toward the valve during a single transcatheter advancement.

14. The apparatus according to claim 13, wherein the catheter is shaped to provide a lumen along a longitudinal axis thereof, and wherein the catheter provides an arrangement for the placing of the first and second segments in the lumen of the catheter, linearly along the longitudinal axis in a manner in which one of the segments is disposed distally to the other segment.

15. The apparatus according to claim 1, wherein:
the first segment defines a first lateral wall that surrounds the first lumen,
the second segment defines a second lateral wall that surrounds the second lumen,
for each of the first and second lateral walls of each segment, the lateral wall has a first and a second portion, and the segment is shaped to provide a channel extending from the first portion to the second portion, and
the apparatus further comprises a flexible longitudinal guide member configured to be removably coupled to a portion of the wall of the segment in a vicinity of the channel.

16. The apparatus according to claim 15, further comprising an anchoring structure, wherein the anchoring structure is disposed at a distal end of the guide member, and wherein the distal end of the guide member is coupled to the portion of the wall of the segment.

17. The apparatus according to claim 12, wherein a diameter of the bar is greater than the distance between the proximal rotational subunits, and wherein during an attempt to corkscrew the proximal rotational subunits around the bar:
the bar restricts the proximal rotational subunits from being corkscrewed into tissue of the patient by applying a counterforce to a torque applied to the helical element in response to rotation thereof, and
the proximal rotational subunits are configured to expand radially in response to the counterforce applied by the bar.

18. The apparatus according to claim 17, further comprising a hollow tube configured to:
be reversibly coupled to the helical element,
push the anchoring structure toward the annuloplasty structure, and
provide torque to the helical element in response to rotation of the tube, and
wherein the helical element is configured to be detached from the hollow tube in response to the radial expansion of the proximal rotational subunits.

19. The apparatus according to claim 1, wherein the annuloplasty structure comprises an annuloplasty ring.

20. The apparatus according to claim 1, further comprising one or more flexible longitudinal guide members, each guide member configured to be removably coupled to respective portions of the annuloplasty structure, and wherein the annuloplasty structure and the one or more guide members are configured to be simultaneously advanced toward the valve of the patient.

21. The apparatus according to claim 1, wherein the annuloplasty structure comprises a partial annuloplasty ring.

22. The apparatus according to claim 1, wherein:
the annuloplasty structure has at least first and second free ends,
a first end of the first segment defines the first free end of the annuloplasty structure, and
a first end of the second segment defines the second free end of the annuloplasty structure.

23. The apparatus according to claim 10, wherein:
the straight configuration of the first and second segments defines a longitudinal axis of the annuloplasty structure,
at least a portion of the annuloplasty structure is shaped to define one or more compressible units, and
wherein the compressible units are compressible in parallel with the longitudinal axis.

24. The apparatus according to claim 23, wherein the compressible units are compressible in response to an application of a pulling force applied to one or more control wires selected from the group consisting of: the first control wire and the second control wire.

25. The apparatus according to claim 1, wherein:
the first segment has a first lateral wall that defines the first lumen,
the second segment has a second lateral wall that defines the second lumen, and
the first and second lateral walls are discrete from each other.

26. The apparatus according to claim 1, wherein the first and second segments are discrete from each other.

27. The apparatus according to claim 1, wherein:
the first segment has first and second ends that define first and second ends, respectively, of the first lumen,
the second segment has first and second ends that define first and second ends, respectively, of the second lumen, and
one end of the first segment is positioned corresponding to a nearest end of the second segment in a manner in which a logitudinal axis of the first lumen at the end of the first segment is disposed at a non-zero angle with respect to a longitudinal axis of the second lumen at the nearest end of the second segment, when the first and second slidable coupling arrangements facilitate control by the control wires of the relative dispositions of the first and second segments.

28. The apparatus according to claim 1, wherein:
the first segment has first and second ends that define first and second ends, respectively, of the first lumen,
the second segment has first and second ends that define first and second ends, respectively, of the second lumen, and
one end of the first segment is positioned corresponding to a nearest end of the second segment in a manner in which one end of the first lumen faces a nearest end of the second lumen.

* * * * *